United States Patent
Lee et al.

(10) Patent No.: US 11,781,908 B2
(45) Date of Patent: Oct. 10, 2023

(54) OPTICAL SENSOR MODULE AND POWER CONTROL METHOD THEREOF

(71) Applicant: Samsung Electronics Co., Ltd., Gyeonggi-do (KR)

(72) Inventors: Jeehoon Lee, Gyeonggi-do (KR); Jungpil Moon, Gyeonggi-do (KR); Inho Yun, Gyeonggi-do (KR); Jiwoon Jung, Gyeonggi-do (KR); Seongmin Je, Gyeonggi-do (KR)

(73) Assignee: Samsung Electronics Co., Ltd., Suwon-si (KR)

(*) Notice: Subject to any disclaimer, the term of this patent is extended or adjusted under 35 U.S.C. 154(b) by 10 days.

(21) Appl. No.: 17/541,358

(22) Filed: Dec. 3, 2021

(65) Prior Publication Data
US 2022/0090962 A1 Mar. 24, 2022

Related U.S. Application Data

(63) Continuation of application No. PCT/KR2020/007209, filed on Jun. 3, 2020.

(30) Foreign Application Priority Data

Jun. 5, 2019 (KR) .......................... 10-2019-0066546

(51) Int. Cl.
*G01J 1/44* (2006.01)
*G01J 1/08* (2006.01)
(Continued)

(52) U.S. Cl.
CPC . *G01J 1/44* (2013.01); *G01J 1/08* (2013.01); *A61B 5/021* (2013.01);
(Continued)

(58) Field of Classification Search
CPC .... G01S 7/4814; G01S 7/4813; G01S 7/4817; G01S 7/486; G01S 17/931; G01S 17/89;
(Continued)

(56) References Cited

U.S. PATENT DOCUMENTS

2012/0133636 A1   5/2012 Kita
2019/0290135 A1*  9/2019 Otaki ................. A61B 5/14551
2019/0366114 A1  12/2019 Kim

FOREIGN PATENT DOCUMENTS

JP    2012-119069 A    6/2012
JP    2014-220969 A   11/2014
(Continued)

*Primary Examiner* — Tony Ko
(74) *Attorney, Agent, or Firm* — Cha & Reiter, LLC

(57) ABSTRACT

According to certain embodiments, an electronic device comprises: a housing; an optical sensor module disposed in the housing and including one or more light-emitting elements, and one or more light-receiving elements; a light source driver disposed in the housing and configured to control power supply of the one or more light-emitting elements; and at least one processor disposed in the housing and operatively connected to the optical sensor module and the light source driver, wherein the at least one processor is configured to identify a light source of the one or more light-emitting elements and turn-on/off timings of the one or more light-emitting elements according to a sensor measurement mode or a measurement function when the optical sensor module is driven, configure a control signal of the light source driver in response to the identified turn-on/off timings of the one or more light-emitting elements, based on the control signal, apply an output voltage of the light source driver as power of the one or more light-emitting elements in a turn-on period of the one or more light-emitting elements, and block the power of the one or more light-emitting elements by limiting output of the light source driver in a turn-off period of the one or more light-emitting elements.

15 Claims, 15 Drawing Sheets

(51) Int. Cl.
    *A61B 5/021*     (2006.01)
    *A61B 5/024*     (2006.01)
    *A61B 5/145*     (2006.01)
    *A61B 5/1455*     (2006.01)

(52) U.S. Cl.
    CPC ....... *A61B 5/02416* (2013.01); *A61B 5/14532* (2013.01); *A61B 5/14551* (2013.01)

(58) Field of Classification Search
    CPC .... G02B 7/021; G02B 26/121; G02B 26/105; G02B 26/124; G02B 27/123
    See application file for complete search history.

(56) References Cited

FOREIGN PATENT DOCUMENTS

| KR | 10-2017-0065401 A | 6/2017 |
| KR | 10-2018-0054521 A | 5/2018 |
| KR | 10-2018-0122526 A | 11/2018 |
| KR | 10-1957258 B1 | 3/2019 |
| WO | 2018/123676 A1 | 7/2018 |

\* cited by examiner

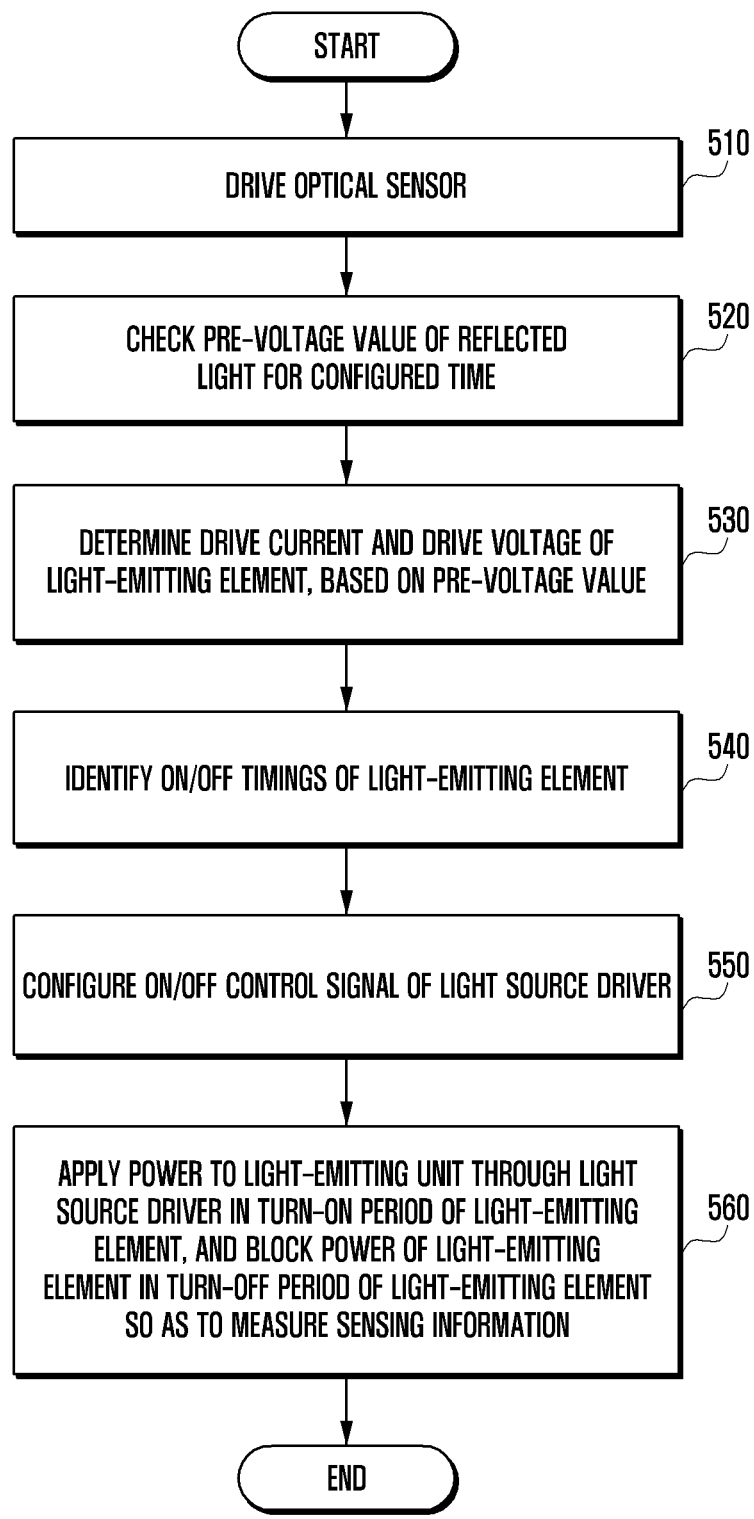

FIG. 12
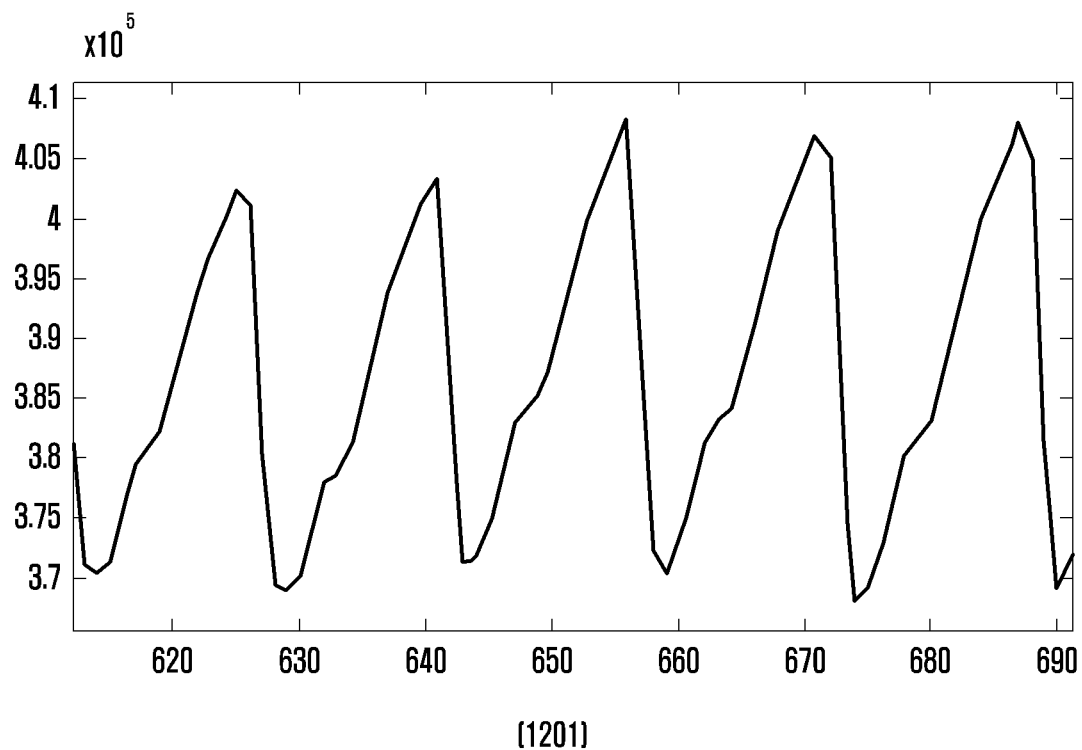
(1201)
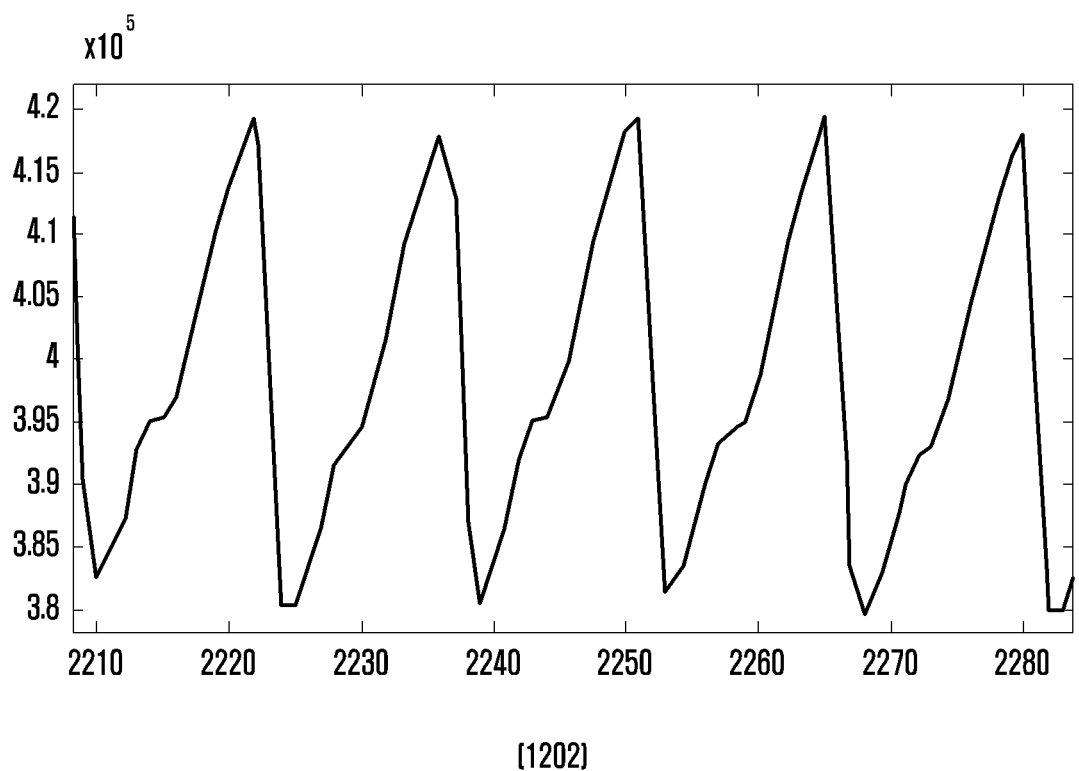
(1202)

OPTICAL SENSOR MODULE AND POWER CONTROL METHOD THEREOF

CROSS-REFERENCE TO RELATED APPLICATION(S)

This application is a continuation of International Application No. PCT/KR2020/007209, filed on Jun. 3, 2020, which claims priority to Korean Patent Application No. 10-2019-0066546, filed on Jun. 5, 2019 in the Korean Intellectual Property Office, the disclosures of which are herein incorporated by reference.

TECHNICAL FIELD

Certain embodiments of the disclosure relate to an optical sensor module including light-emitting and light-receiving elements and a method for controlling power thereof.

BACKGROUND ART

Electronic devices support complex management of various functions in line with development of hardware and software technologies. In addition, electronic devices may provide users with various functions or services based on information collected through sensors.

For example, an electronic device may include an optical sensor device including at least one light-emitting element and/or light-receiving element. In addition, the electronic device may use the optical sensor device so as to determine whether an object approaches or to measure the electronic device user's heartbeat, stress, blood oxygen saturation (SpO2), blood pressure, or blood glucose information. The optical sensor may include a light-emitting element in various output bands (for example, Green, Red, blue, IR, and the like), and may measure various biometric information according to a combination of output bands.

SUMMARY

The light-emitting element has different voltages applied thereto, depending on the type of the light-emitting element and the drive current. The electronic device uses a boost convertor so as to control power supplied to the light-emitting element. The boost convertor boosts an input voltage applied thereto. This generates a high voltage output voltage as compared with the input voltage. The high voltage output is used for a variety of purposes such as a LED driver and a battery charger. However, the boost convertor is always-on regardless of whether device receiving the high voltage is operating. This results in unnecessary power consumption.

Certain embodiments may provide an optical sensor module and a method for controlling power thereof, wherein output of a light source driver (for example, boost convertor) is selectively transferred to a light-emitting element or blocked, in response to an operation signal of the light-emitting element. Accordingly, the current consumption resulting from the boost convertor can be reduced.

According to certain embodiments, an electronic device comprises: a housing; an optical sensor module disposed in the housing and comprising one or more light-emitting elements, and one or more light-receiving elements; a light source driver disposed in the housing and configured to control power supply of the one or more light-emitting elements; and at least one processor disposed in the housing and operatively connected to the optical sensor module and the light source driver, wherein the at least one processor is configured to identify a light source of the one or more light-emitting elements and turn-on/off timings of the one or more light-emitting elements according to a sensor measurement mode or a measurement function when the optical sensor module is driven, configure a control signal of the light source driver in response to the identified turn-on/off timings of the one or more light-emitting elements, based on the control signal, apply an output voltage of the light source driver as power of the one or more light-emitting elements in a turn-on period of the one or more light-emitting elements, and block the power of the one or more light-emitting elements by limiting output of the light source driver in a turn-off period of the one or more light-emitting elements.

According to certain embodiments, an electronic device comprise an optical sensor module, the electronic device comprising an optical sensor module and a light source driver, the optical sensor module comprising: one or more light-emitting elements; one or more light-receiving elements; a signal processing circuit configured to control driving of the light emitting elements and the one or more light-receiving elements; and at least one processor, the light source driver being configured to control power supply of the at least one light-emitting element, wherein the signal processing circuit is configured to, when the optical sensor module is driven, under a control of the at least one processor, configure a control signal of the light source driver in response to a light source of the one or more light-emitting elements and a turn-on/off timing signal of the one or more light-emitting elements according to a sensor measurement mode or a measurement function, wherein the signal processing circuit is configured to, based on the control signal, apply an output voltage obtained by boosting an input voltage through the light source driver as power of the one or more light-emitting elements in turn-on period of the one or more light-emitting elements, wherein the signal processing circuit is configured to block the power of the one or more light-emitting elements by limiting output of the light source driver in turn-off period of the one or more light-emitting elements, and wherein the signal processing circuit is configured to transmit a signal collected based on the one or more light-receiving elements to the at least one processor.

An optical sensor device according to certain embodiments may control a light source driver such that, in a turn-on period of one or more light-emitting elements, a boosted output voltage is provided as power of the one or more light-emitting elements through the light source driver, and in a turn-off period of the one or more light-emitting elements, power supply provided from the light source driver is blocked, thereby reducing power consumption without degrading performance of the optical sensor.

BRIEF DESCRIPTION OF DRAWINGS

FIG. 5 illustrates a power control method of an optical sensor device according to an embodiment;

FIG. 12 illustrates sensing information output data of an optical sensor device according to certain embodiments.

MODE FOR THE INVENTION

It should be appreciated that certain embodiments of the present disclosure and the terms used therein are not intended to limit the technological features set forth herein to particular embodiments and include various changes, equivalents, or replacements for a corresponding embodiment. Therefore, the scope of the present invention should be construed as including all changes or modifications derived based on the technical spirit of the present invention in addition to the embodiments disclosed herein are included in the scope of the present invention.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

Figure 1:
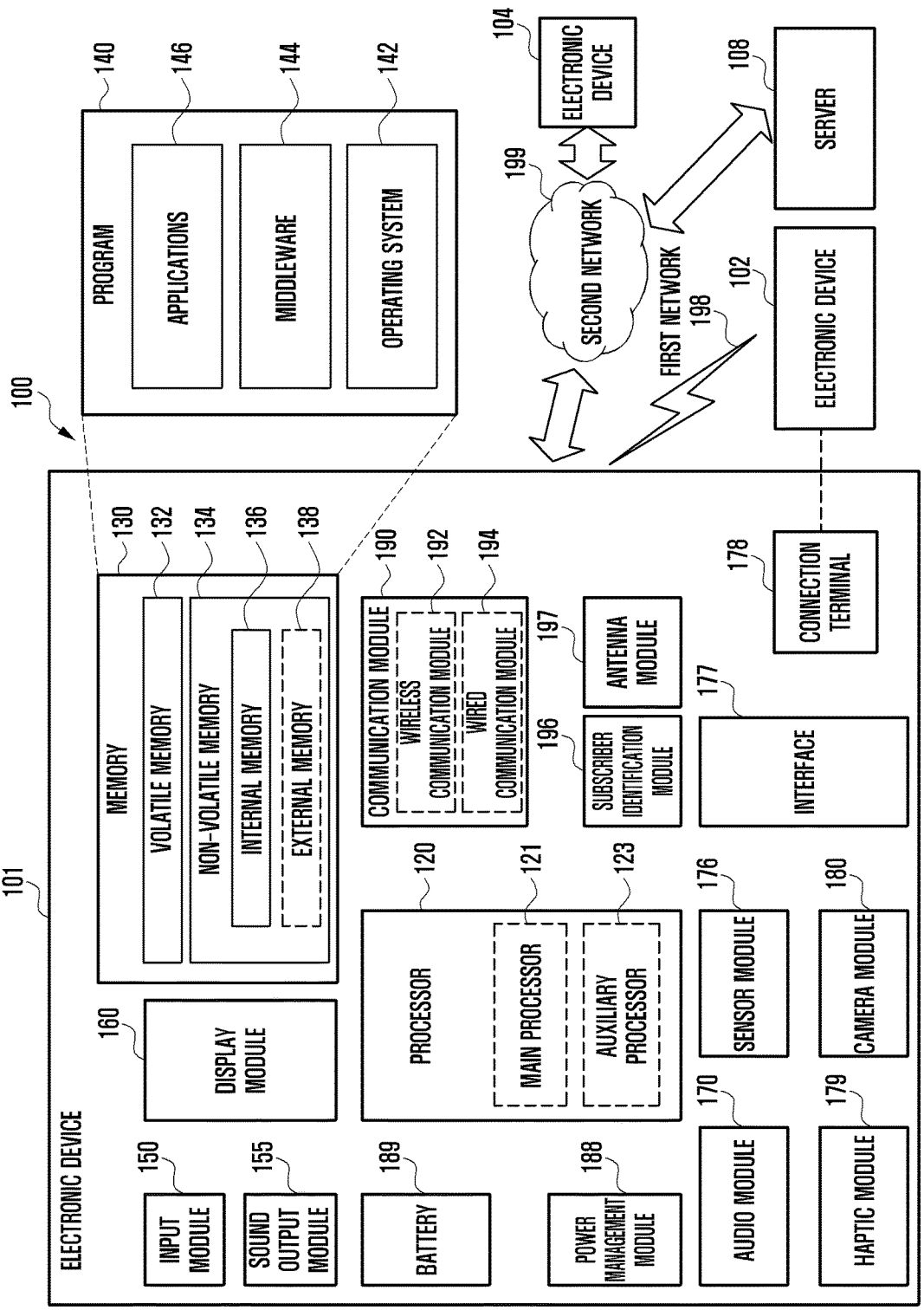
FIG. 1 is a block diagram of an electronic device in a network environment according to certain embodiments.

FIG. 1 is a block diagram illustrating an electronic device 101 in a network environment 100 according to certain embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. The term "processor" shall be understood to refer to both the singular and plural contexts. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 and/or the non-volatile memory 134. The non-volatile memory 134 may include an internal memory 136 and/or an external memory 138.

The program 140 may be stored in the memory 130 as software, and may include, for example, an operating system (OS) 142, middleware 144, and/or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other.

The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101.

According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

According to some embodiments, a sensor module 176 may acquire external environmental information or biometric information. An electronic device may detect at least one of humidity, temperature, heat quantity, illuminance, light, ion, vibration, radiation, sound waves, ultrasonic waves, pressure, chemical components, or biological reactions through the sensor module 176.

According to some embodiments, the sensor module 176 may include an optical sensor device incorporating at least one of an illuminance sensor, a proximity sensor, a color sensor (e.g., red, green, and blue (RGB) sensor), an infrared (IR) sensor, a biometric sensor, a heart rate monitor (HRM) sensor, a photoplethysmography (PPG) sensor, and an iris recognition sensor. The optical sensor device may measure at least one piece of information of a heart rate, a fingerprint, an iris, brain waves, a face, blood pressure, or blood sugar.

A number of the sensors in the sensor module 176 use a combination of Light Emitting Diodes (LEDs) and photodiodes. The LEDs convert electrical power to light. Photodiodes convert light to electrical power. In a sensor, LEDs can be used to emit light which can be reflected off of an object. The object can be, for example, a fingertip. The photodiodes receive the reflected light and can measure various things, based on the reflected light. The sensors are commonly on the surface of the housing. In the case of sensors that use light, the sensors that use light are commonly disposed on the surface of the housing, such that emitted light can be emitted outside the housing, and light reflected from an object outside the housing can be received in the housing.

Figure 2A:
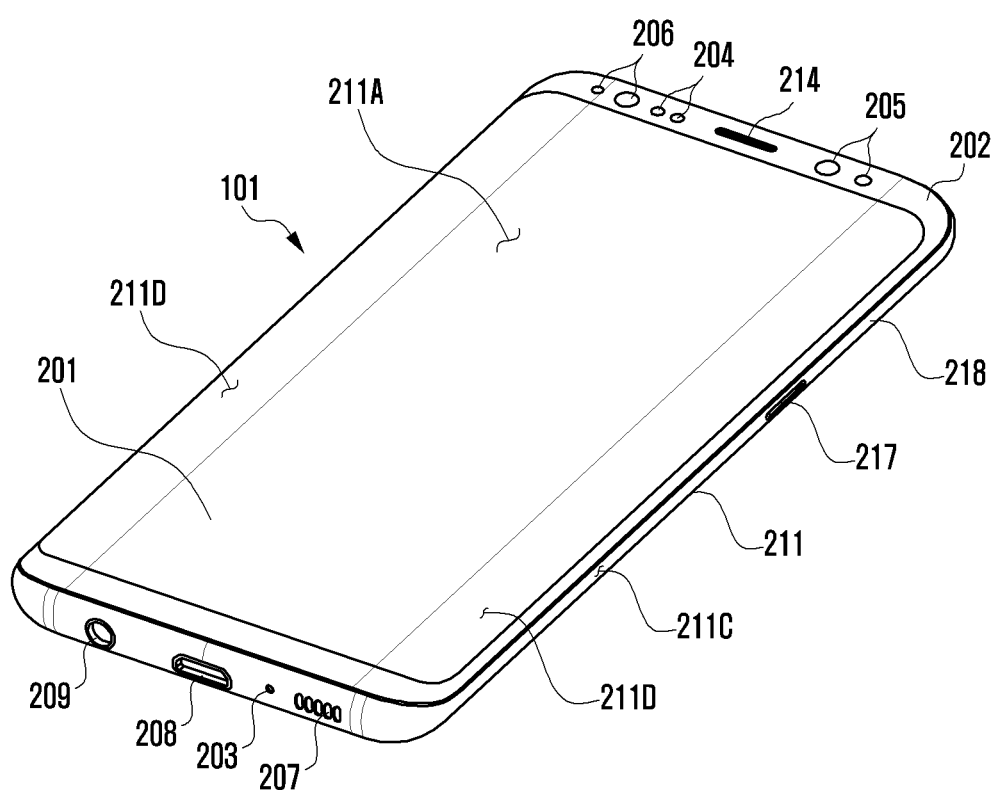
FIGS. 2A and 2B are a front perspective view and a rear perspective view of an electronic device according to certain embodiments.
Figure 2B:
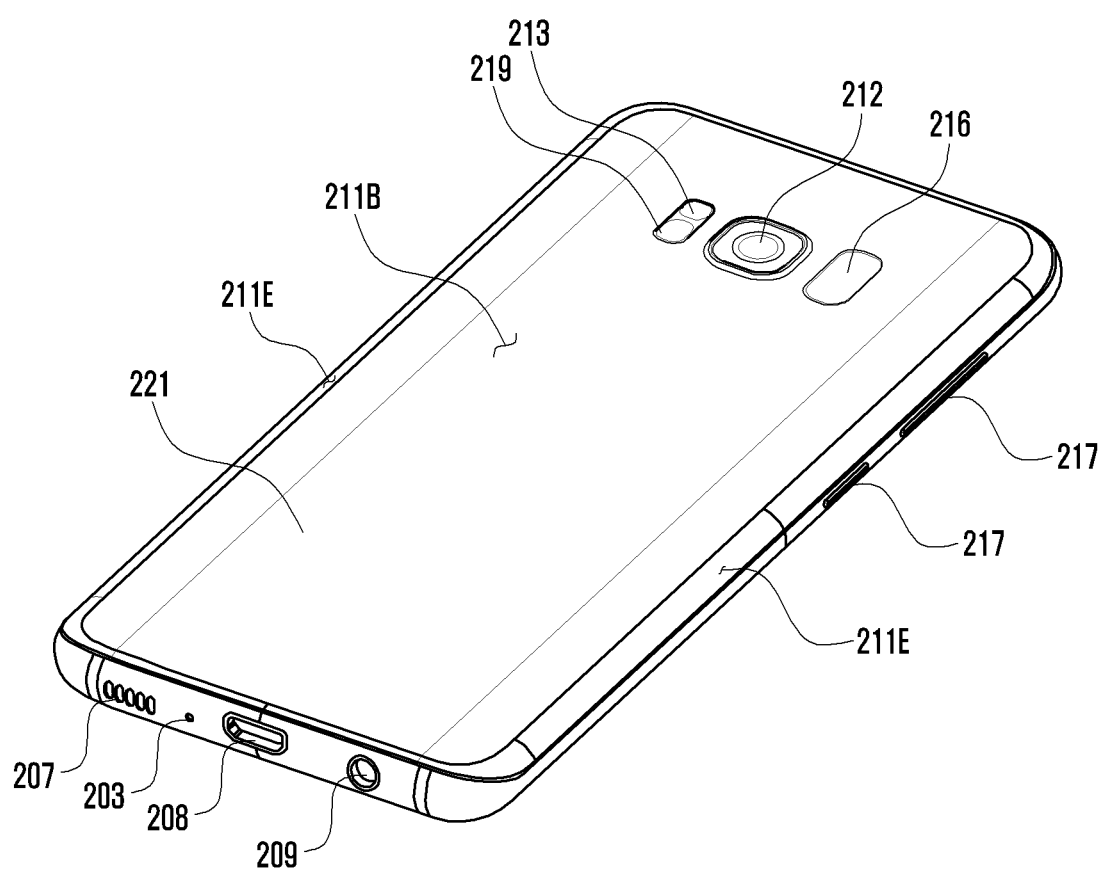

FIGS. 2A and 2B describe the housing of an electronic device. The electronic device can include a sensor module 204 on the front and sensors modules 216, and 219 on the rear. The sensor modules 204, 216, and 219 may include an optical sensor device. The location and numbers of sensor module are not limited to the foregoing and other embodiments may have fewer or more sensors modules and sensor modules in different locations. The optical sensor device may convert an electrical signal to light and output the same, or may convert received light into an electrical signal.

FIGS. 2A and 2B are a front perspective view and a rear perspective view of an electronic device 101 according to certain embodiments.

Referring to FIGS. 2A and 2B, the electronic device 101 according to an embodiment may include an optical sensor device (e.g., a biometric sensor, a proximity sensor, etc.) (e.g., the sensor module 176 of FIG. 1).

As shown in FIGS. 2A and 2B, the electronic device 101 including the optical sensor device according to an embodiment may be a smart phone. The electronic device 101 may include a housing 211 including a first surface (or front surface) 211A, a second surface (or rear surface) 211B, and a side surface 211C surrounding the space between the first surface 211A and the second surface 211B. In another embodiment (not shown), the housing may refer to a structure which configures a part of the first surface 211A, the second surface 211B, and the side surface 211C of FIG. 1. The first surface 211A may be formed by a front plate 202 (e.g., a polymer plate or a glass plate including various coating layers), at least a part of which is substantially transparent. The second surface 211B may be formed by a rear plate 211 which is substantially opaque. The rear plate 221 may be formed of, for example, coated or colored glass, ceramic, polymer, or metal (e.g., aluminum, stainless steel (STS), or magnesium), or a combination of two or more of these materials. The side surface 211C may be formed by a side bezel structure (or a "side member") 218 coupled to the front plate 202 and the rear plate 221 and including a metal and/or a polymer. In some embodiments, the rear plate 211 and the side bezel structure 218 may be integrally configured and may include the same material (e.g., a metal material such as aluminum).

In the illustrated embodiment, the front plate 202 may include, at opposite long edges of the front plate 202, two first areas 211D, which are bent from the first surface 211A toward the rear plate 211 and extend seamlessly. The front plate 202 (or the rear plate 211) may include only one of the first areas 211D (or the second areas 211E).

The electronic device 101 may include at least one of a display 201, audio modules 203, 207, and 214, sensor modules 204, 216, and 219, camera modules 205, 212, and 213, key input devices 217, a light-emitting element 206, and connector holes 208 and 209. In some embodiments, the electronic device 101 may not include at least one (e.g., the key input devices 217 or the light-emitting element 206) of the components, or may additionally include another component.

For example, the display 201 may be exposed through a significant part of the front plate 202. In some embodiments, at least a part of the display 201 may be exposed through the front plate 202 configuring the first areas 211D of the side surface 211C and the first surface 211A.

The audio modules 203, 207, and 214 may include a microphone hole 203 and speaker holes 207 and 214. The microphone hole 203 may include a microphone disposed therein so as to acquire external sound, and in some embodiments, the microphone hole may include multiple microphones disposed therein so as to detect the direction of sound. The camera modules 205, 212, and 213 may include a first camera device 205 disposed on the first surface 211A of the electronic device 101, a second camera device 212 disposed on the second surface 211B, and/or a flash 213. The flash 213 may include, for example, a light-emitting diode or a xenon lamp. The key input devices 217 may be disposed on the side surface 211C of the housing 211. In another embodiment, the electronic device 101 may not include some or all of the above-mentioned key input devices 217, and a key input device 217, which is not included therein, may be implemented in another form such as a soft key on the display 201. In some embodiments, the key input devices may include a sensor module 216 disposed on the second surface 211B of the housing 211. The connector holes 208 and 209 may include a first connector hole 208 capable of receiving a connector (e.g., a USB connector) for transmitting or receiving power and/or data to or from an external electronic device, and/or a second connector hole (e.g., an earphone jack) 209 capable of receiving a connector for transmitting or receiving an audio signal to or from an external electronic device.

In some embodiments, at least a part of the sensor modules 204 and 219 and/or at least a part of the key input devices 217 may be disposed in the first areas 211D and/or the second areas 211E.

In another embodiment, the light-emitting element 206 may provide a light source which is interlocked with, for example, an operation of the camera module 205. The light-emitting element 206 may include, for example, an LED, an IR LED, and a xenon lamp.

The sensor module 204, 216, and 219 may generate an electrical signal or a data value corresponding to an internal operating state of the electronic device 101 or an external environment state. The sensor modules of the electronic device 101 may further include, for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor 204.

According to an embodiment, the sensor modules 204, 216, and 219 may include an optical sensor device. The optical sensor device may convert an electrical signal to light and output the same, or may convert received light into an electrical signal. According to an embodiment, an optical sensor device 310 may be a photoplethysmography (PPG) sensor. The electronic device is not limited to a smartphone. In certain embodiments, the electronic device can include a smart watch. A smart watch can have a housing that is about the size of the human wrist with straps that can be fastened around the forearm.

Figure 3A:
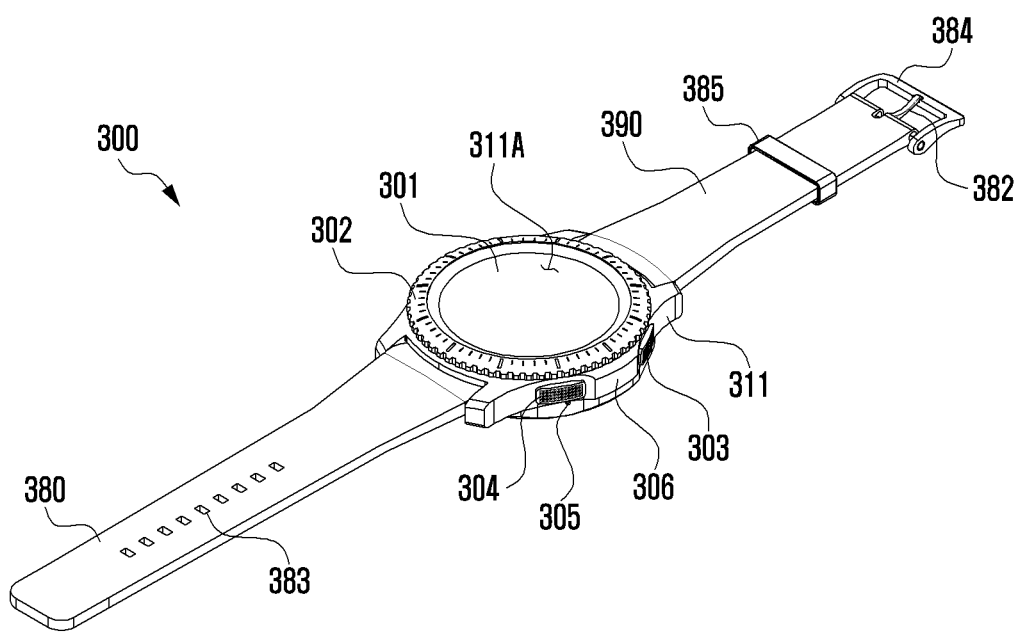
FIGS. 3A and 3B are a front perspective view and a rear perspective view of an electronic device according to certain embodiments.
Figure 3B:
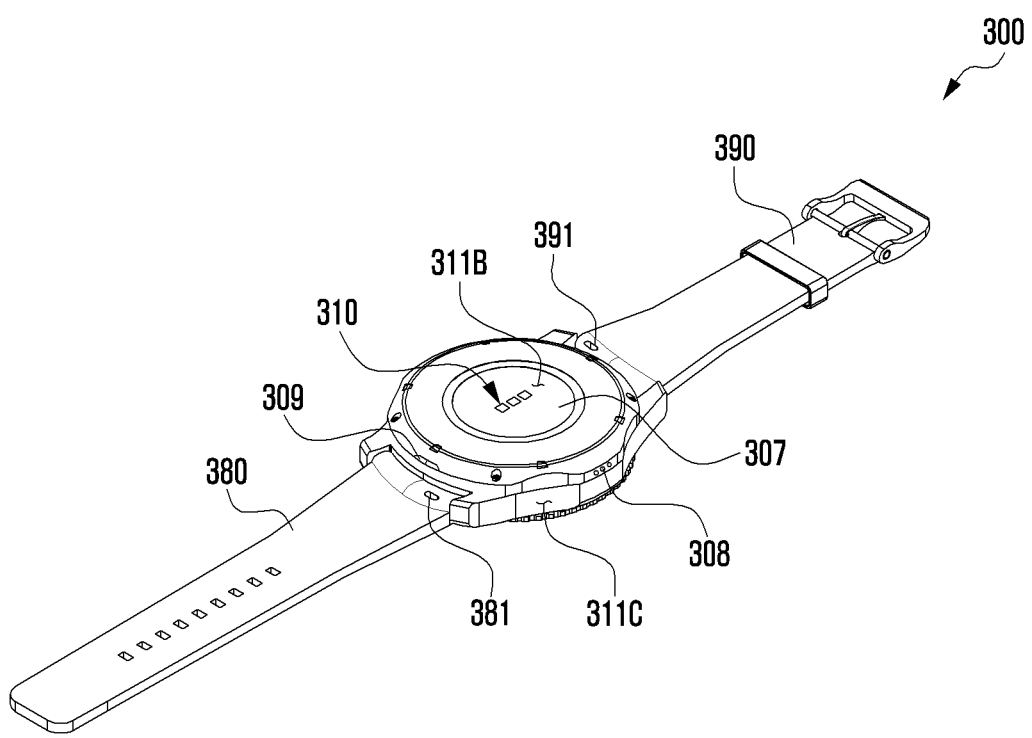

FIGS. 3A and 3B are a front perspective view and a rear perspective view of an electronic device 300 according to certain embodiments.

Referring to FIGS. 3A and 3B, as shown in FIG. 3A, the electronic device 300 (e.g., the electronic device 101 of FIG. 1) according to an embodiment may be a wrist wearable device (e.g., a watch-type, bracelet-type, band-type, or bangle-type device). According to an embodiment, in a case where the electronic device 300 is a wearable device, as shown in FIG. 3B, the optical sensor device 310 may be exposed on a rear surface 311B (e.g., the surface that comes into contact with a user's body when the user wears the electronic device) of the electronic device.

The electronic device 300 (e.g., the electronic device 101 of FIG. 1) according to an embodiment may include a housing 311 including a first surface (or a front surface) 311A, a second surface (or a rear surface) 311B, and a side surface 311C surrounding the space between the first surface 311A and the second surface 311B, and coupling members 380 and 390 connected to at least a part of the housing 311 and configured to detachably couple the electronic device 300 to a part (e.g., a wrist or an ankle) of a user's body. According to an embodiment, the first surface 311A may be formed by a front plate 301 (e.g., a polymer plate or a glass plate including various coating layers), at least a part of which is substantially transparent. The second surface 311B may be formed by a rear plate 307 which is substantially opaque. The side surface 311C may be formed by a side bezel structure (or a "side member") 306 coupled to the front plate 301 and the rear plate 307 and including a metal and/or a polymer.

According to an embodiment, the electronic device 300 may include at least one of a display 320 (e.g., the display device 160 of FIG. 1), audio modules 305 and 308, a sensor module 310, and key input device 302, 303, and 304, and a connector hole 309. In some embodiments, the electronic device 300 may not include at least one (e.g., the key input devices 302, 303, and 304, the connector hole 309, or the sensor module 310) of the components, or may additionally include another component.

The shape of the display 320 may be a shape corresponding to the shape of the front plate 301, and may have various shapes such as a circle, an oval, or a polygon. The display 320 may be coupled to or disposed adjacent to a touch detection circuit, a pressure sensor capable of measuring the intensity (pressure) of a touch, and/or a fingerprint sensor.

The key input devices 302, 303, and 304 may include a wheel key 302 disposed on the first surface 311A of the housing 311 and rotatable in at least one direction, and/or side key buttons 303 and 304 disposed on the side surface 311C of the housing 311. The wheel key may have a shape corresponding to the shape of the front plate 302.

The coupling members 380 and 390 may be detachably coupled to at least a partial area of the housing 311 by using locking members 381 and 391. The coupling members 380 and 390 may include one or more of a fixing member 382, a fixing member fastening hole 383, a band guide member 384, and a band fixing ring 385. The fixing member 382 may be configured to fix the housing 311 and the coupling members 380 and 390 to a part (e.g., a wrist, an ankle, etc.) of a user's body. The fixing member fastening hole 383 may correspond to the fixing member 382 to fix the housing 311 and the coupling members 380 and 390 to a part of a user's body. The band guide member 384 may be configured to limit a range of movement of the fixing member 382 when the fixing member 382 is fastened to the fixing member fastening hole 383, so that the coupling members 380 and 390 are in close contact with a part of a user's body to be coupled. The band fixing ring 385 may limit a range of movement of the coupling members 380 and 390 in a state in which the fixing member 382 and the fixing member fastening hole 383 are fastened to each other. The coupling members 380 and 390 may have various materials and shapes. A woven fabric, leather, rubber, urethane, metal, ceramic, or a combination of at least two of the above materials may be used to form an integrated unit link and a plurality of unit links to be movable with respect to each other.

According to an embodiment, the sensor module 310 may generate an electrical signal or a data value corresponding to an internal operating state of the electronic device 300 or an external environment state. According to an embodiment, the sensor module 310 may include an optical sensor device. The optical sensor device may be exposed to the outside from the rear surface 311B of the electronic device 300 to output light to an external object (e.g., a living body), and detect reflected light reflected from the external object. According to an embodiment, the optical sensor device may be a photoplethysmography (PPG) sensor. The PPG sensor may detect, by a light-receiving element (e.g., a photodiode), reflected light reflected by an external object (e.g., a living body) among light output from a light-emitting element (e.g., an LED), and measure at least one piece of biometric information among blood pressure, heart rate, oxygen saturation in blood, vascular elasticity, blood flow velocity, blood sugar, and the degree of arteriosclerosis, based on the reflected light detected by the light-receiving element.

Figure 4:
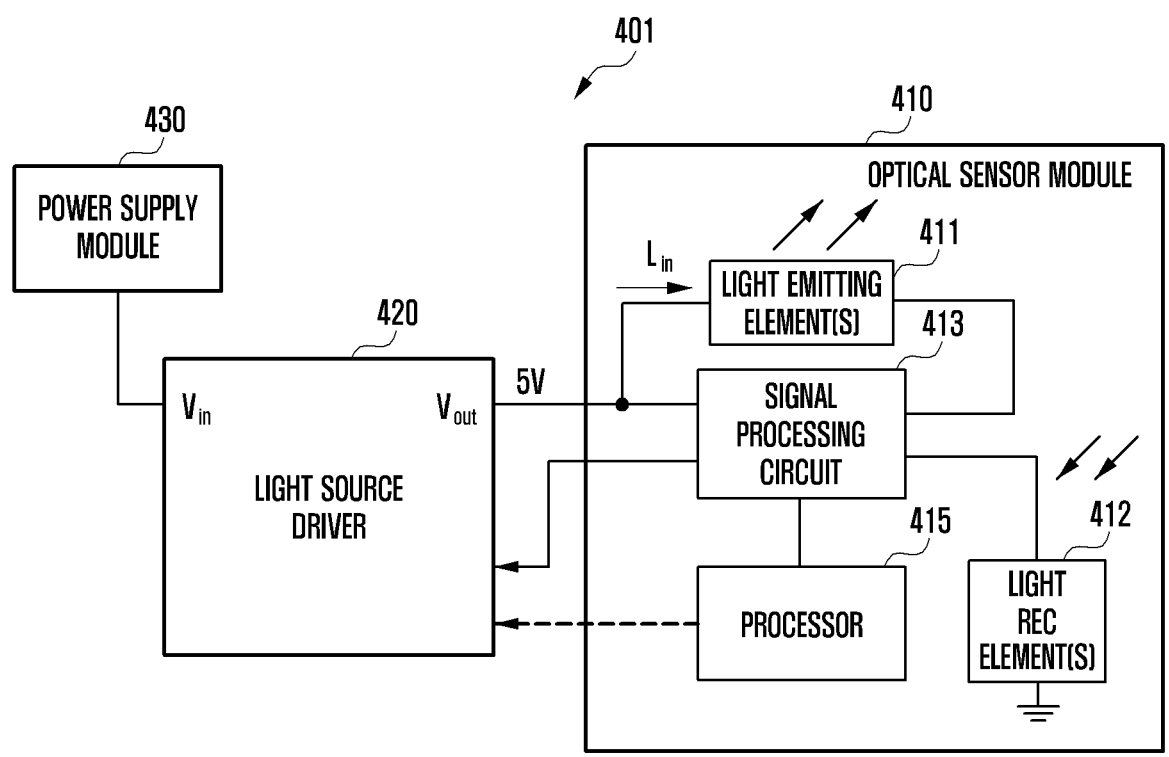
FIG. 4 illustrates an example of an electronic device including an optical sensor module according to certain embodiments.

Many of the aforementioned sensor modules include one or more light-emitting elements 411, and one or more light-receiving elements 412 as is shown in FIG. 4. The light emitting elements 411 emit light that is reflected by an external object. The reflected light is received by the light receiving elements 412 and converted to an electronic signal. The signal processing circuit 413 processes the electronic signal and provides the processed electronic signal to the processor.

A light source driver 420 boosts power received from the power supply module 430 (Vin) to an output voltage (Vout) that drives the one or more light emitting elements 411. However, the light emitting element 411 does not always need to emit light. In some embodiments, a processor 415 transmits a signal to the signal processing circuit 413, notifying that the sensor will be used. Accordingly, the signal processing circuit 413 controls the light source driver 420 to provide power to the light emitting elements 411 to emit light according to turn-on timing of the one or more light emitting elements 411. In other embodiments, the foregoing can be performed by the processor 415. FIG. 4 illustrates an example of an electronic device including an optical sensor module according to certain embodiments.

Referring to FIG. 4, an electronic device 401 (e.g., the electronic device 101 of FIG. 1, the electronic device 101 of FIGS. 2A and 2B, and the electronic device 300 of FIGS. 3A and 3B) according to an embodiment may include a light sensor module 410, a light source driver 420, and a power supply module 430 (e.g., a battery).

The optical sensor module 410 may include one or more light-emitting elements 411, one or more light-receiving elements 412, a signal processing circuit (e.g., analog front end (AFE)) 413, and a processor 415.

The processor 415 of the optical sensor module 410 may control the one or more light-emitting elements 411, the one or more light-receiving elements 412, and the signal processing circuit 413. Additionally, the processor 415 may generate and control a signal for controlling the operations of the light source driver 420 and the power supply module 430.

The processor 145 may be included in the optical sensor module, but is not limited thereto, and may be replaced with the processor 120 of FIG. 1. When replaced with the processor 120 of FIG. 1, the processor 120 of FIG. 1 may control the operations of the one or more light-emitting elements 411, the one or more light-receiving elements 412, and the signal processing circuit 413 of the optical sensor module 410, the light source driver 420, and the power supply module 430.

The processor 415 included in the optical sensor module may operate in conjunction with the processor of FIG. 1. For example, the processor 120 of FIG. 1 may control the light source driver 420 and the power supply module 430, and the processor 415 of the optical sensor module may control the one or more light-emitting elements 411, the one or more light-receiving elements 412, and the signal processing circuit 413. In this case, the processor of FIG. 1 may include an application processor, and the processor of the optical sensor module may include a micro controller unit.

The optical sensor module 410 may include a photoplethysmogram (PPG) sensor, but is not limited to one. The optical sensor module 410 may be mounted inside the electronic device 401 and may be disposed in such a manner that a part thereof (for example, a light-emitting element and a light-receiving element) is exposed to the outside through a housing (or a cover glass) of the electronic device.

The optical sensor module 410 may emit light by the one or more light-emitting elements 411 and receive reflected light or light by the one or more light-receiving elements 412 to measure information (e.g., biometric information/bio-signal) related to the electronic device 401, the outside of the electronic device 401, or a user. The optical sensor module 410 may include a light source (e.g., a light-emitting element) which emits light in various wavelength bands or colors to measure various pieces of information. The optical sensor module 410, under the control of the processor 415, output light of a different wavelength from among a plurality of light sources according to a bio-signal to be measured or a user function, or receive reflected light or light through different photodiodes.

More specifically, the one or more light-emitting elements 411 at least one light source among a light-emitting diode (LED), a semiconductor laser (laser diode (LD)), a solid laser, and an infrared (IR) diode. The light-emitting diode may include at least a part of a red LED, a green LED, and a blue LED having different wavelength characteristics. For example, a light source of a green wavelength is a wavelength band used to measure a heart rate of the human body, and may have a characteristic resistant to noise since the same penetrates shallowly into skin. A light source of a red wavelength penetrates deeply into skin of the human body and may be used to measure a heart rate more accurately. A light source using an infrared (IR) wavelength may be used to acquire biometric information such as a heart rate of the human body and saturation of percutaneous oxygen (SPO2). A light source of a blue wavelength may be used to measure the tendency of blood sugar. The optical sensor module 410 may be able to measure skin tone when red, green, and infrared wavelengths are used as a light source. The optical sensor module 410 may be implemented to acquire more pieces of biometric information including light sources of various LED wavelength bands.

The type and number of light-emitting elements may be changed according to a sensor measurement service or a biometric measurement mode provided by the electronic device. According to some embodiments, the one or more light-receiving elements 412 may be implemented as a light-receiving element having the same sensitivity (e.g., a gain according to a wavelength) according to wavelength characteristics of a light-emitting element implemented in the electronic device.

The one or more light-receiving elements 412 may include a light-receiving element, for example, a photo diode (PD). Alternatively, the light receiving elements can include a photoresistors, or phototransistors. The one or more light-receiving elements 412 may obtain light reflected from an external object (e.g., a living body) and transmit a received signal to the signal processing circuit 413.

The signal processing circuit 413 may control the light source driver 420 to operate the one or more light-emitting elements 411, and process the received signal transmitted from the one or more light-receiving elements 412. The signal processing circuit 413 can perform the foregoing in response to a signal (such as a biometric signal) from the processor 415. Additionally, the signal processing circuit 413 can provide the processed received signal (from the one or more light-receiving elements 412) to the processor 415. The signal processing circuit 413 may include an analog front-end (AFE) circuit.

The signal processing circuit 413 may control the amount of light and turn-on/off timings of the one or more light-emitting elements 411 through the light source driver 420. The turn-on/off timings may be different according to a wavelength band of a light source that emits light or a sensing measurement mode. The signal processing circuit 413 may configure a control signal of the light source driver 420 according to the turn-on/off timings, and control the operation of the light source driver 420 according to the control signal. The control signal may include an enable signal, but is not limited thereto.

During the turn-on timing, the signal processing circuit 413 may transmit an enable signal to the light source driver 420 such that the light source driver 420 boosts an input voltage to apply an output voltage as power of the one or more light-emitting elements 411. During the turn-off timing, the signal processing circuit 413 blocks the output voltage applied to the one or more light-emitting elements 411. For example, based on the enable signal, the light source driver 420 may output the boosted voltage to the one or more light-emitting elements 411 when an output signal is high, and may not output the voltage when the output signal is low.

The signal processing circuit 413 may use a switch circuit according to the turn-on/off timings of the one or more light-emitting elements 411 so as to control such that the light source driver 420 operates to boost an input voltage and output the same to the one or more light-emitting elements 411, or the voltage transmitted to the one or more light-emitting elements 411 is not output. For example, the one or more light-emitting elements 411 may receive power (e.g., an output voltage of the light source driver) from the light source driver 420 at the turn-on timing, and may not receive power from the light source driver 420 at the turn-off timing.

The signal processing circuit 413 may amplify and process a signal (e.g., a current) output from the one or more light-receiving elements 412, and transmit the signal to the processor 415. The signal processing circuit 413 may include at least one of a signal amplifier, a noise filter, and an analog-to-digital (AD) converter. The signal processing circuit 413 may amplify an analog signal transmitted from the one or more light-receiving elements 412 by the signal amplifier, remove noise by the noise filter, convert the analog signal into a digital signal by the AD converter, and transmit the converted digital signal to the processor 415.

The light source driver 420 may provide a drive power to the light-emitting element or block power supply under the control of the processor 415. In this case, during turn-on timings, the processor 415 may configure a control signal of the light source driver 420 such that, based on the control signal, the light source driver 420 boosts an input voltage to apply an output voltage to the one or more light-emitting elements 411 as power. During, and blocks the power supplied to the one or more light-emitting elements 411 in a turn-off period of the one or more light-emitting elements 411.

A subject of the operation of controlling the light source driver 420 may be the processor 415 or the signal processing circuit 413 according to implementation when the electronic device is manufactured.

The light source driver 420 may generate a drive power of the one or more light-emitting elements 411 and transmit the generated drive power to the one or more light-emitting elements 411. The light source driver 420 may be under the control of the signal processing circuit 413 or the processor 415. The light source driver 420 may include one of a boost converter type, a buck converter type, a buck-boost converter type, and an AC-DC switching mode power supply (SMPS) circuit. An output terminal of the light source driver 420 may be connected to an input terminal of the light-emitting element included in the one or more light-emitting elements 411.

The light source driver 420 may generate a drive power of the light-emitting element by boosting an input voltage VIN transmitted from the power supply module 430 to an output voltage VOUT required to drive the light-emitting element. The output voltage may be power required for driving each light-emitting element. For example, a green LED may require a drive voltage of approximately 5 V, and a red LED may require a drive voltage of approximately 2.2 V.

The light source driver 420 may output or may not output a voltage to the one or more light-emitting elements 411 under the control of the signal processing circuit 413 or the processor 415.

The light source driver 420 may receive an input voltage or may not receive an input voltage under the control of the signal processing circuit 413 or the processor 415.

The power supply module 430 may convert power (e.g., an external voltage or a battery voltage) into a DC voltage and provide the DC voltage to the light source driver 420 as an input voltage Vin. The external power may be a voltage provided from an external charging device, and the battery voltage may be a supply voltage of a battery.

The processor 415 may control the light sensor module 410 and determine a light source of the one or more light-emitting elements 411 according to a sensor measurement mode or a measurement function, and identify the turn-on/off timings of the light-emitting element to transmit the same to the signal processing circuit 413. The processor 415 may include a micro controller unit (MCU), but is not limited thereto.

The processor 415 may analyze data, based on a measurement signal transmitted from the signal processing circuit 413, so as to identify sensing information (e.g., biometric information). For example, the processor 415 may extract various signal parameters such as a peak and the number of signals per unit time, based on a signal measured from the one or more light-receiving elements 412, and analyze the signal parameters to measure at least one piece of biometric information among blood pressure, heart rate, oxygen saturation in blood, vascular elasticity, blood flow velocity, blood sugar, and the degree of arteriosclerosis.

The processor 415 may configure a control signal of the light source driver 420 in response to the turn-on/off timings of the light-emitting element, and control the light source driver 420 such that, based on the control signal, the light source driver 420 boosts an input voltage in a turn-on period of the light-emitting element so as to provide power to the one or more light-emitting elements 411, and blocks the power provided to the one or more light-emitting elements 411 in a turn-off period of the one or more light-emitting elements 411.

Hereinafter, operations of the optical sensor device will be described. The operations of the optical sensor device may be performed by the processor 415 or the signal processing circuit 413 of FIG. 4.

FIG. 5 illustrates a power control method of an optical sensor device according to an embodiment.

Referring to FIG. 5, in operation 510, an optical sensor device (e.g., a biosensor) included in an electronic device (e.g., the electronic device 101 of FIG. 1, the electronic device 101 of FIGS. 2A and 2B, the electronic device 300 of FIGS. 3A and 3B, and the electronic device 401 of FIG. 4) may be driven for sensing (e.g., biometric information). For example, a processor of the electronic device may detect a biometric event and control the optical sensor device to be driven in response to the biometric event. A biometric event can a request by the user for biometric data by selection of an application.

In operation 520, the optical sensor device may identify a pre-voltage value (e.g., an ADC value) of reflected light for a configured time in response to a biometric signal. For example, photodiodes generate some power when receiving light. This power can be used to determine the amount of power to apply to the at least one light emitting elements 411. For example, if at least one light emitting elements 411 are known to need a specified amount of power, the amount of power from the photodiodes can be subtracted, and the difference can be provided by the light source driver 420.

The optical sensor device may emit light to the outside through a light-emitting unit for a configured time (e.g., 1 to 2 seconds) before acquiring biometric data, and receive reflected light reflected by an external object (e.g., a living body) through a light-receiving unit. The optical sensor may do this to identify a pre-voltage value for determining an optimal current (e.g., a forward current) of a light-emitting element. A light source of the light-emitting unit may be different according to a measurement mode or a measurement function of an optical sensor. For example, the optical sensor device may use an IR diode and a red LED as a light-emitting element to measure oxygen saturation, and may use a blue LED to measure blood sugar. Alternatively, in a case of a wearable device which is directly attached to the body, a green LED may be implemented as a light-emitting element. In a case of an LED, since the amount of light emission is determined according to a current value, the process of identifying the pre-voltage value may be a part of a pre-configuration process for determining the amount of light of a light-emitting element according to the characteristics of an external object.

In operation 530, the optical sensor device may determine a drive current (e.g., an optimal current) and a drive voltage of the light-emitting element, based on the pre-voltage value. Operations 520 and 530 are a pre-configuration process for identifying environmental information on a measurement object (e.g., a user) before measuring biometric information, and when the pre-configuration process is already performed, operations 520 and 530 may be omitted.

In operation 540, the optical sensor device may identify turn-on/off timings of the light-emitting element for acquiring biometric data. The turn-on/off timings of the light-emitting element may be different according to an information measurement mode and measurement function.

In operation 550, the optical sensor device may configure an on/off control signal of a light source driver in response to the turn-on/off timings of the light-emitting element. The optical sensor device may configure such that the light source driver boosts an input voltage in a turn-on period of the light-emitting element, applies the boosted output voltage as a drive power of the light-emitting element, and blocks the power provided to the light-emitting unit in a turn-off period of the light-emitting element.

The optical sensor device may be configured to apply, based on an enable signal, an output voltage boosted by the light source driver as a drive power of the light-emitting element in the turn-on period of the light-emitting element, and to block the power transmitted to the light-emitting element in the turn-off period of the light-emitting element.

The optical sensor device may be configured to supply an input voltage to the light source driver in the turn-on period of the light-emitting element by using a switching circuit and boost the input voltage to apply the same as a drive power of the light-emitting element, and to block the input voltage of the light source driver in the turn-off period of the light-emitting element to block the power transmitted to the light-emitting element.

The optical sensor device may configure an on/off control signal of the light source driver in the same manner as the turn-on/off timings of the light-emitting element. The optical sensor device may operate the light source driver at the same time point as the turn-on timing of the light-emitting element to apply power to the light-emitting element, and restrict the operation of the light source driver at the same time point as the turn-off timing of the light-emitting element to block power supply to the light-emitting element.

According to some embodiments, the optical sensor device may configure an on/off control signal of the light source driver by applying a compensation value for compensating for the difference between an output voltage of the light source driver and a drive voltage of the light-emitting element. For example, the optical sensor device may identify the output voltage of the light source driver, and when the output voltage does not satisfy a drive voltage reference required to drive the light-emitting element, identify and apply a compensation value configured to compensate for the difference between the output voltage of the light source driver and the drive voltage of the light-emitting element, based on previously measured test data. For example, the compensation value may be a time parameter for the turn-on period, but is not limited thereto, and may be an input voltage parameter applied to the light source driver. Alternatively, the optical sensor device may apply the compensation value, based on another parameter.

In operation 560, the optical sensor device may apply power to the light-emitting unit through the light source driver in the turn-on period of the light-emitting element according to the on/off control signal of the light source driver, and block the power to the light-emitting unit in the turn-off period of the light-emitting element to measure sensing information (e.g., biometric information). For example, the optical sensor device may boost a voltage input through the light source driver in the turn-on period to apply the output voltage as power of the light-emitting unit, and block the power applied to the light-emitting unit in the turn-off period.

Figure 6A:
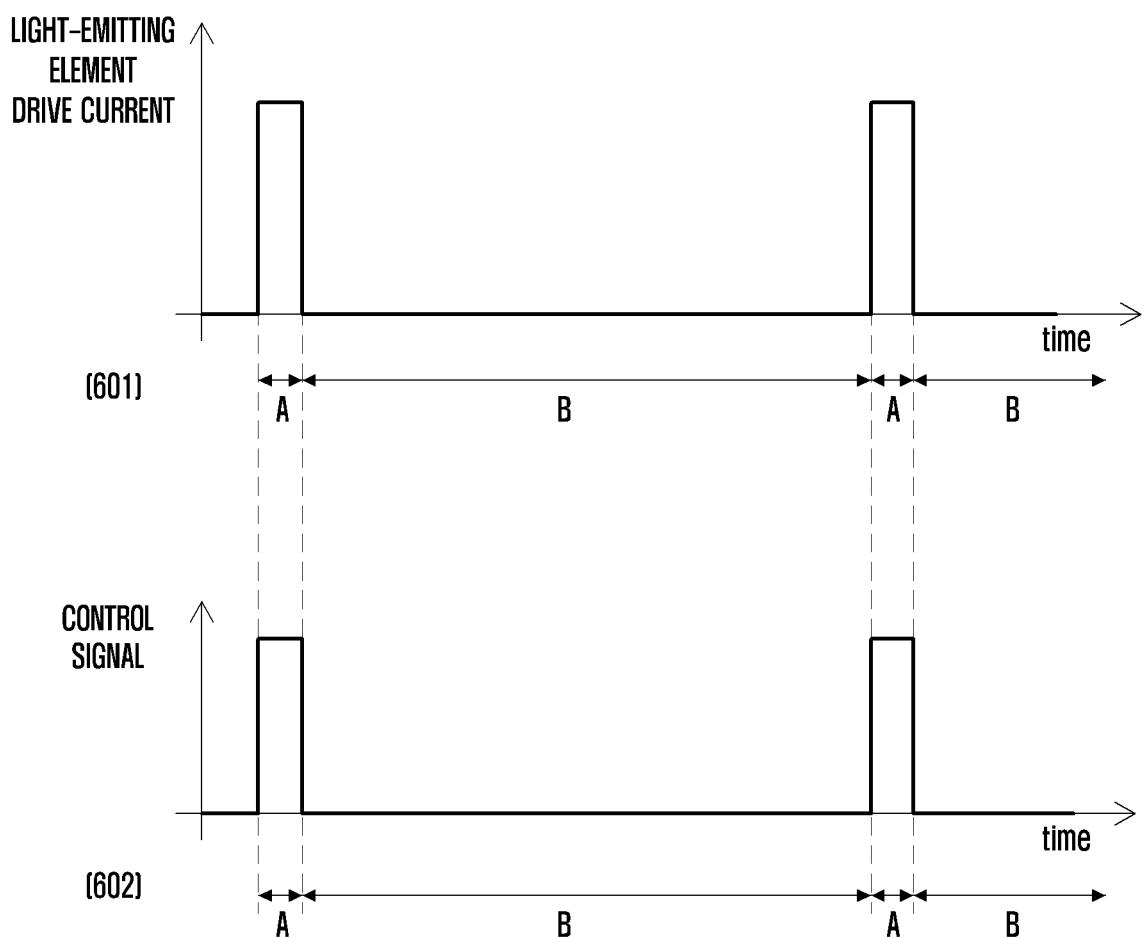
FIGS. 6A and 6B illustrate waveforms indicating a drive current of a light-emitting element and a control signal of a light source driver according to an embodiment.
Figure 6B:
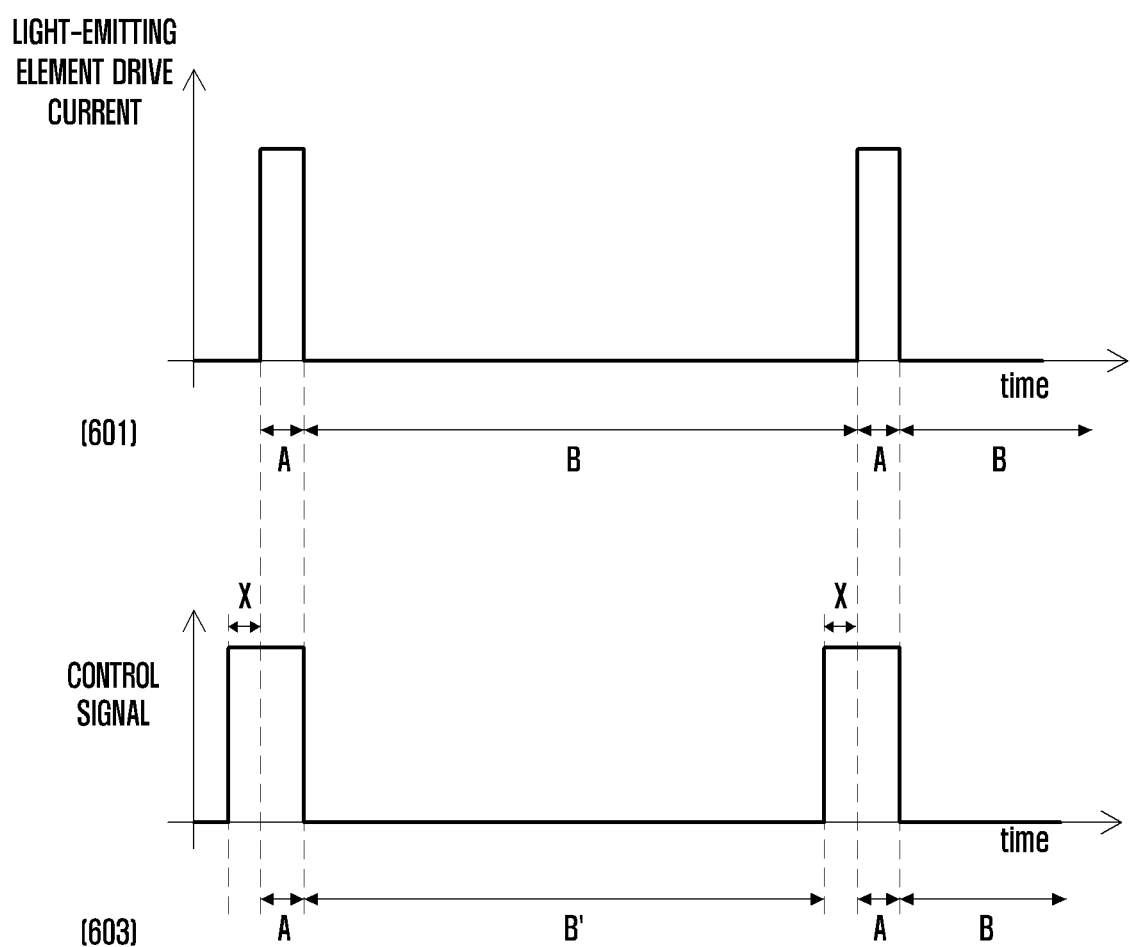

FIGS. 6A and 6B illustrate waveforms indicating a drive current 601 of a light-emitting element and control signals 602 and 603 of a light source driver according to an embodiment.

FIGS. 6A and 6B show turn on/off timings of the light emitting elements 412. According to one embodiment, the light source driver 420 can receive the control signal 602. As can be seen, the duty pulse corresponds to the turn on timings. However, a different power may be needed for example, generating light of particular wavelengths. Accordingly, a compensation X can be added to the duty pulse.

Referring to FIGS. 6A and 6B, according to an embodiment, an optical sensor device may selectively supply power of a light-emitting unit by turning on/off the light source driver in response to turn-on/off timings of the light-emitting element for biometric measurement.

A drive current waveform of the light-emitting element may be the waveform shown in FIG. 6A. In the example of FIG. 6A, the light-emitting element may operate with a duration having a turn-on A period in which light is emitted and a turn-off B period in which light is not emitted. The turn-on period A may indicate a high signal, and the turn-off period B may indicate a low signal. The optical sensor device may selectively control the light source driver to generate a drive voltage (e.g., an output voltage) in the turn-on period A and apply power to the light-emitting element, and to block power supply to the light-emitting element in the turn-off period B. When the output voltage transmitted to the light source driver reaches a drive voltage (e.g., a forward voltage) or a drive current, a current flows in the light-emitting element and the light-emitting element may emit light. As shown in FIG. 6A, the optical sensor device may selectively transmit an enable signal (e.g., high) to the light source driver only in the turn-on period A to supply power to the light-emitting unit only in the turn-on period A, and block power supply to the light-emitting unit in the turn-off period B.

The optical sensor device may be implemented such that the light source driver is turned on/off by applying a compensation value. The compensation value compensates for the difference between an applied voltage of the light-emitting element and an output voltage of a power supply circuit corresponding to turn-on/off timings that are used for biometric measurement. For example, an applied voltage needed for driving of the light-emitting element may be different for each wavelength band. For example, a drive voltage of a green LED may be relatively higher than drive voltages of LEDs in other wavelength bands, and a compensation value for generating a high drive voltage may be required. For example, the compensation value may be a time parameter additionally required to boost an input voltage in the light source driver to reach an output voltage, but is not limited thereto, and may also be a voltage parameter which increases an input voltage.

The compensation value may be a compensation value configured based on pre-measured data according to the characteristics of the light-emitting element. For example, the optical sensor device may configure a compensation value as a compensation value determined by (1) applying an input voltage for each light-emitting element in order to analyze the characteristics of the light-emitting element, (2) identifying a boosted output voltage, and (3) testing a compensation value for boosting into the output voltage.

For example, assuming that the compensation value is X in time, as shown in FIG. 6B, the optical sensor device may add X to the turn-on period A of the light-emitting element and drive the light source driver in an A+X period to apply a boosted output voltage as power of the light-emitting unit, and block power supply of the light-emitting unit provided through the light source driver in a turn-off time point of the light-emitting element. According to an embodiment, the optical sensor device may control a voltage to be boosted by the light source driver as much as a drive voltage reference required to drive the light-emitting element by applying a compensation value.

Figure 7:
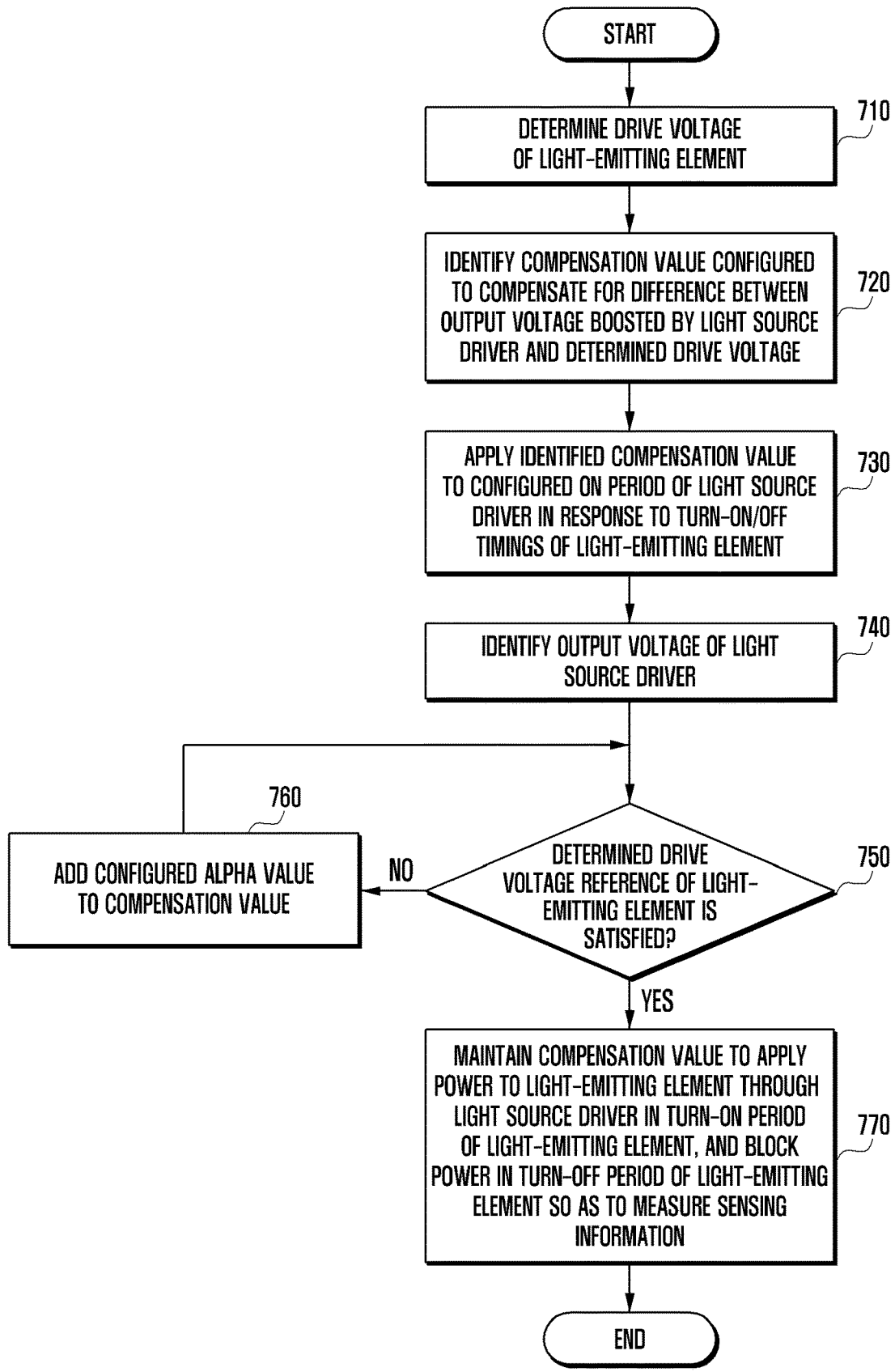
FIG. 7 illustrates a power control method of an optical sensor device according to an embodiment.

FIG. 7 illustrates a power control method of an optical sensor device according to an embodiment.

Referring to FIG. 7, the optical sensor device may determine a drive voltage of a light-emitting element in operation 710. Since the operation of determining the drive voltage of the light-emitting element is the same as operations 510 to 530 of FIG. 5, a detailed description thereof will be omitted. The operation of determining the drive voltage of the light-emitting element may be a pre-configuration operation. For example, the optical sensor device may determine an optimal drive current and drive voltage of the light-emitting element 411 by identifying a pre-voltage value (e.g., an ADC value) of reflected light for a configured time when a sensor is driven. In general, since a measurement value of an optical sensor is different according to a state (e.g., skin color) of a measurement object and surrounding environment information, it is necessary to determine a drive current and a drive voltage of the optical sensor suitable for a measurement situation in order to improve the accuracy of measurement. According to an embodiment, operation 710 may be a pre-configuration operation for determining an optimal drive current and drive voltage for driving the light-emitting element 411 according to a measurement situation, by identifying a state of a measurement object and surrounding environment information in advance, before measuring data.

In operation 720, the optical sensor device may identify a compensation value configured to compensate for the difference between an output voltage boosted by the light source driver and the determined drive voltage. The compensation value may be a compensation value determined by identifying a boosted output voltage for each light-emitting element and testing a compensation value for additionally boosting the output voltage. For example, when the drive voltage is 5 V and the output voltage is 4.75 V, the compensation value may be a compensation value configured according to a test result so that an additional 0.25 V is boosted. According to some embodiments, the optical sensor device may identify a compensation value, based on a compensation value database (or table information) for applying the compensation value.

In operation 730, the optical sensor device may control the operation of the light source driver 420 by applying a compensation value X to control signal 603. The control signal 603 may be configured in response to turn-on/off timings of the light-emitting element. In operation 740, the optical sensor device may identify an output voltage boosted from an input voltage by the light source driver 420.

In operation 750, the optical sensor device may determine whether the output voltage of the light source driver output after applying the compensation value satisfies a drive voltage reference of the light-emitting element. For example, in a case of a green LED, a drive voltage may be 5 V, and the optical sensor device may identify an output voltage of the green LED at the time of biometric measurement using the green LED as a light source, apply a compensation value configured by the difference between the output voltage and the drive voltage, and then identify whether an output voltage of the light source driver is boosted to 5 V and output.

In operation 750, when the output voltage of the light source driver does not satisfy the drive voltage reference of the light-emitting element, the optical sensor device may proceed to operation 760 to additionally apply an alpha value to the compensation value in order to increase the boost, and proceed to operation 750 and repeat until the output voltage of the light source driver reaches the drive voltage reference of the light-emitting element.

In operation 770, when the output voltage of the light source driver satisfies the drive voltage reference of the light-emitting element, the optical sensor device may maintain the compensation value to apply power of the light-emitting element by the output voltage boosted through the light source driver in the turn-on period of the light-emitting element, and operate to block power supply of the light-emitting element provided through the light source driver in a turn-off period of the light-emitting element, so as to measure biometric information.

Figure 8:
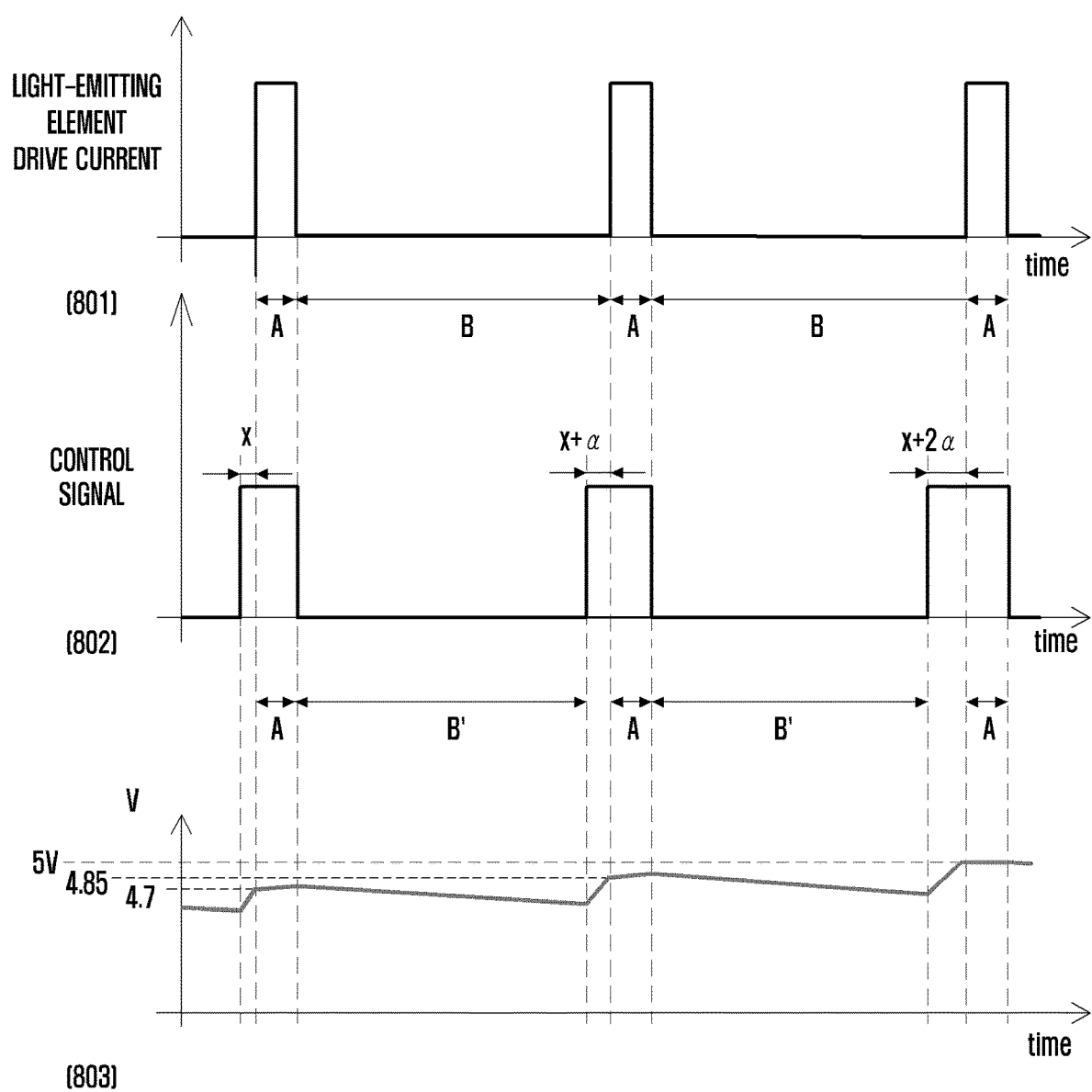
FIG. 8 illustrates a waveform indicating a drive current of a light-emitting element and a control signal and a measurement value of a light source driver according to an embodiment.

FIG. 8 illustrates a waveform indicating a drive current of a light-emitting element 411 and a control signal 802 and a measurement value of a light source driver according to an embodiment.

Referring to FIG. 8, the optical sensor device may increase an alpha value for a compensation value in stages until an output voltage boosted by the light source driver 420 reaches a drive voltage reference of the light-emitting element 411 in a turn-on period of the light-emitting element 411, and apply the same to the next turn-on time of the light-emitting element 411.

For example, a drive current waveform of the light-emitting element may operate with a duration having a turn-on A period in which light is emitted and a turn-off B period in which light is not emitted, as shown in 801. Signal 803 indicates a measurement value of an output voltage output by boosting an input voltage by the light source driver 420. It can be seen that the output voltage when the light-emitting element 411 is firstly turned on is measured to be 4.7 V, the output voltage when the light-emitting element 411 is secondly turned on is measured to be 4.85 V, and the output voltage when the light-emitting element 411 is thirdly turned on is measured to be 5 V.

Signal 802 indicates a control signal of the light source driver 420, as shown in 802, a compensation value X configured to compensate for the difference between 4.7 V and 5 V based on compensation value data may be additionally applied and applied to the first turn-on period of a light-emitting driver, and the output voltage may be identified. When the output voltage to which the compensation value has been applied does not reach the drive voltage reference of the light-emitting element, the optical sensor device may identify the output voltage by applying the compensation value X and an alpha value c, as in the second turn-on period. When the output voltage of the second turn-on period does not reach the drive voltage reference of the light-emitting element, as in the third turn-on period, the optical sensor device may apply a value of 2α to the compensation value X to operate the light source driver 420, and such a process can be repeated until the output voltage reaches the drive voltage reference, and when the drive voltage reference is reached, the optical sensor device may maintain the compensation value to supply power to the light-emitting element through the light source driver or to block power supply.

Figure 9:
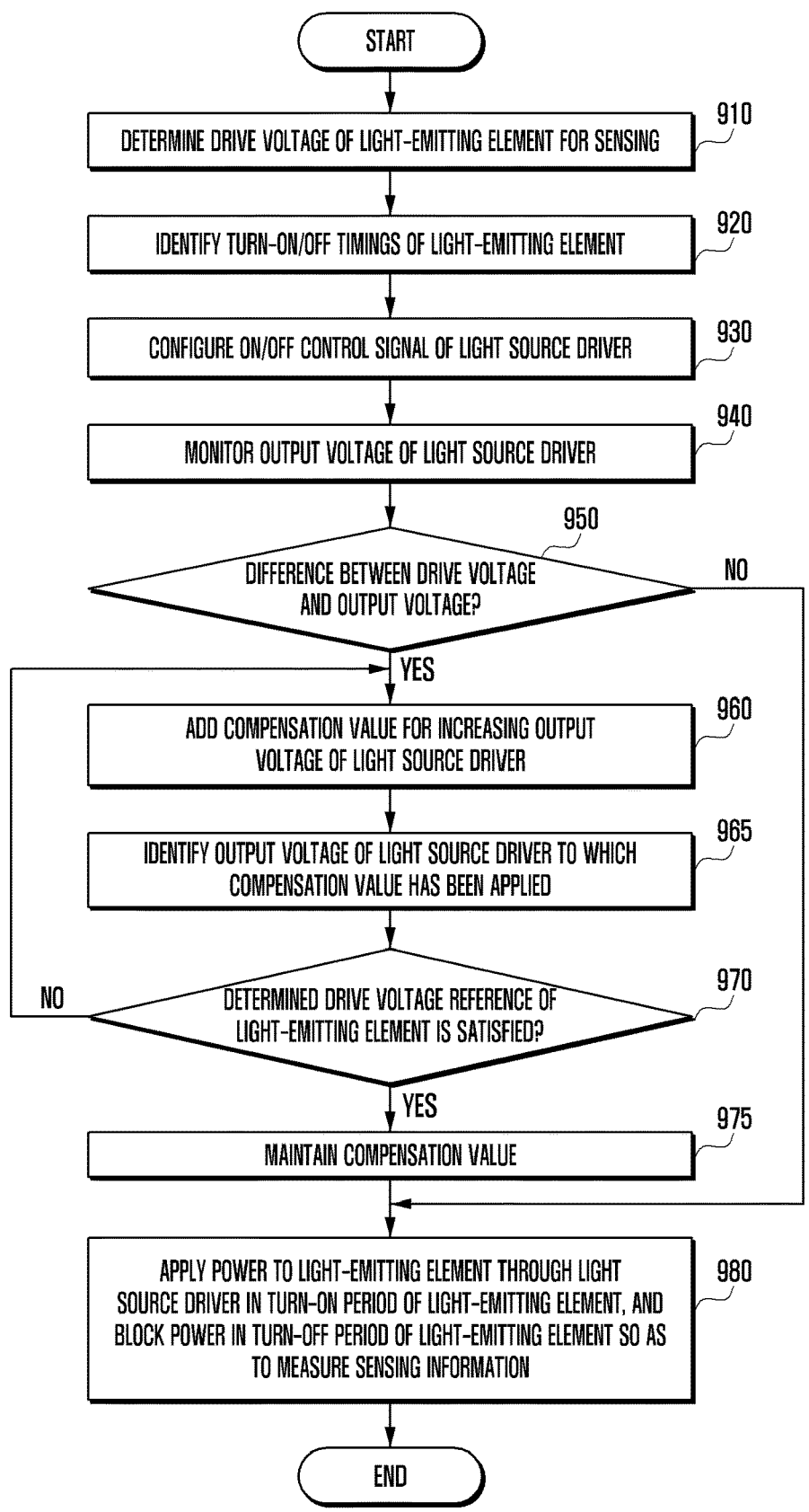
FIG. 9 illustrates a power control method of an optical sensor device according to an embodiment.

FIG. 9 illustrates a power control method of an optical sensor device according to an embodiment.

Referring to FIG. 9, according to an embodiment, the optical sensor device may determine a drive voltage of a light-emitting element 411 in operation 910. Since the operation of determining the drive voltage of the light-emitting element is the same as operations 510 to 530 of FIG. 5, a detailed description thereof will be omitted.

In operation 920, the optical sensor device may identify turn-on/off timings of the light-emitting element 411, based on the determined drive voltage.

In operation 930, the optical sensor device may configure an on/off control signal 802 of a light source driver 420 in response to the turn-on/off timings of the light-emitting element 411.

In operation 940, the optical sensor device may monitor an output voltage of the light source driver 420 to measure the output voltage boosted by an input voltage.

In operation 950, the optical sensor device may calculate whether a difference exists between the output voltage of the light source driver and the drive voltage of the light-emitting element 411. When there is no difference between the output voltage of the light source driver 420 and the drive voltage, the optical sensor device may proceed to operation 980, and control to apply power to the light-emitting element in a turn-on period of the light-emitting element 411 through the light source driver 420 and block the power in a turn-off period, so as to measure sensing information.

In operation 960, the optical sensor device may configure the light source driver 420 to operate by adding a compensation value for compensating for the difference between the output voltage and the drive voltage.

In operation 965, the optical sensor device 420 may measure and identify the output voltage of the light source driver to which the compensation value has been applied. In operation 970, the optical sensor device may determine whether the output voltage of the light source driver 420 to which the compensation value has been applied satisfies a drive voltage reference of the light-emitting element 411. When the output voltage of the light source driver 420 satisfies the drive voltage reference of the light-emitting element, the optical sensor device may configure the light source driver to operate by maintaining the compensation value as in operation 975.

When the output voltage of the light source driver 420 does not satisfy the drive voltage reference of the light-emitting element 411, the optical sensor device may proceed to operation 960 and repeat the operation of additionally applying the compensation value until the drive voltage reference of the light-emitting element is reached.

In operation 980, when the output voltage of the light source driver 420 satisfies the drive voltage reference of the light-emitting element 411, the optical sensor device may control to apply power to the light-emitting element 411 through the light source driver 420 in the turn-on period of the light-emitting element 411 and block the power of the light-emitting element 411 supplied through the light source driver 420 in the turn-off period of the light-emitting element 411, so as to measure sensing information.

Figure 10:
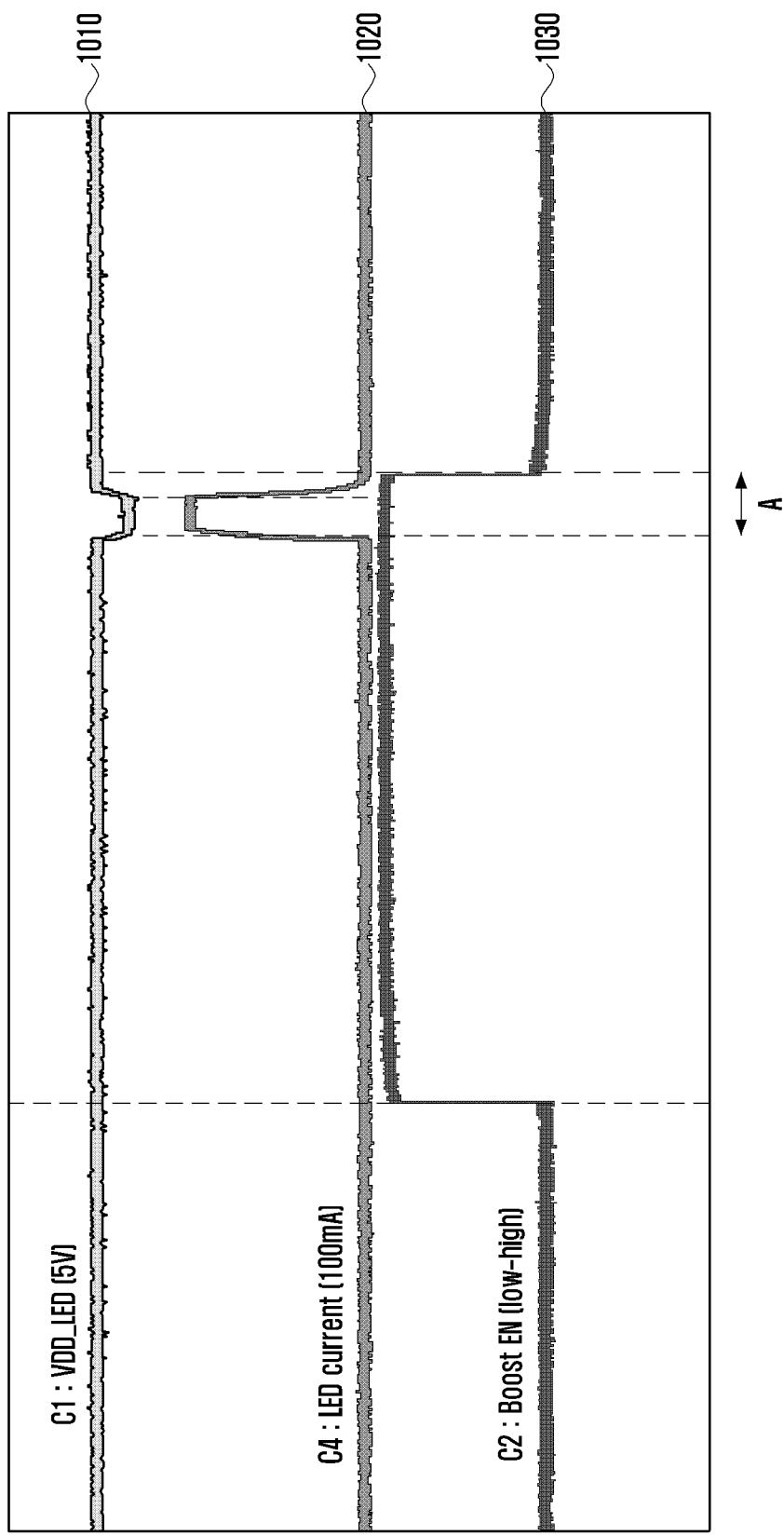
FIG. 10 illustrates measurements of a voltage and a current of a light-emitting element and an operation signal of a light source driver according to an embodiment.

FIG. 10 illustrates measurements of a voltage and a current of a light-emitting element and an operation signal of a light source driver according to an embodiment.

Referring to FIG. 10, according to an embodiment, an optical sensor module may maintain a voltage value of the light-emitting element 411 even when the light source driver 420 selectively operates according to turn-on/off timings of the light-emitting element. According to an embodiment, 1010 indicates a voltage flow of the light-emitting element, 1020 indicates a current flow of the light-emitting element 411, and 1030 indicates a control signal (e.g., an enable signal) of the light source driver 420. The light-emitting element 411 may be turned on in a period A, and the light-emitting element 411 may be turned off in periods other than A. As shown in 1020, the turn-on period A is a high period and is thus a period in which the light-emitting element 411 emits light, and a low period is a turn-off period of the light-emitting element 411. As shown in 1030, it can be seen that the light source driver 420 according to an embodiment of the disclosure starts an operation by configuring an enable signal as a high signal before the turn-on timing of the turn-on period A, and blocks power supply to the light-emitting element 411 by configuring the enable signal as a low signal later than the turn-off period. However, as shown in 1010, since the light-emitting element 411 does not consume a current even when the light source driver is turned off by a low signal, it can be seen that a voltage value (e.g., 5 V) charged in a capacitor of the light-emitting element is maintained even in the turn-on period A.

Figure 11:
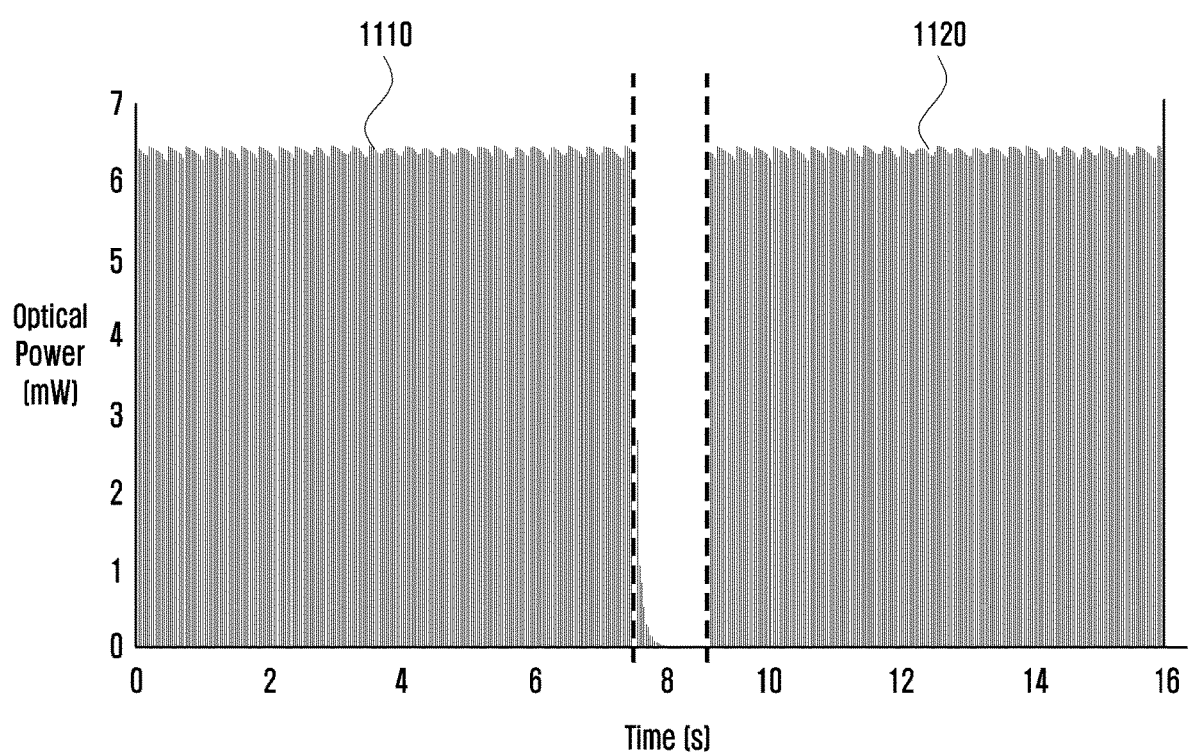
FIG. 11 illustrates data obtained by measuring the amount of light of a light-emitting element according to an embodiment.

FIG. 11 illustrates data obtained by measuring the amount of light of a light-emitting element according to an embodiment.

Referring to FIG. 11, it can be seen that there is no difference in the amount of light of the light-emitting element 411 in relation to the case 1110 of selectively controlling the operation of a light source driver 420 as in certain embodiments and the case 1120 of always driving the light source driver. The case 1110 indicates the amount of LED light which is measured after controlling the light source driver to operate at a turn-on timing of the light-emitting element and the light source driver not to operate at a turn-off timing of the light-emitting element, as in certain embodiments of the disclosure, and 1120 indicates the amount of LED light which is measured by always operating the light source driver regardless of the turn-on/off timings of the light-emitting element. In this way, a drive voltage required for driving the light-emitting element may be selectively provided by selectively controlling the operation of the light source driver 420, and biometric information can be accurately measured while minimizing current consumption by causing the light-emitting element to emit light or not to emit light at a predetermined timing for biometric measurement.

FIG. 12 illustrates sensing information output data of an optical sensor device according to certain embodiments.

Referring to FIG. 12, as in certain embodiments, the optical sensor device can reduce current consumption and improve the efficiency of a light source driver by selectively controlling the operation of the light source driver. 1201 indicates a biometric information waveform measured by controlling the light source driver to operate at a turn-on timing of a light-emitting element and the light source driver not to operate at a turn-off timing of the light-emitting element, as in the disclosure, and 1202 indicates a biometric information waveform measured by always operating the light source driver regardless of the turn-on/off timings of the light-emitting element. As described above, it can be seen that biometric information measurement performance is not deteriorated even by controlling the light source driver to operate at the turn-on timing of the light-emitting element and the light source driver not to operate at the turn-off timing of the light-emitting element as in certain embodiments of the disclosure.

According to certain embodiments, an electronic device comprises: a housing; an optical sensor module disposed in the housing and comprising one or more light-emitting elements, and one or more light-receiving elements; a light source driver disposed in the housing and configured to control power supply of the one or more light-emitting elements; and at least one processor disposed in the housing and operatively connected to the optical sensor module and the light source driver, wherein the at least one processor is configured to identify a light source of the one or more light-emitting elements and turn-on/off timings of the one or more light-emitting elements according to a sensor measurement mode or a measurement function when the optical sensor module is driven, configure a control signal of the light source driver in response to the identified turn-on/off timings of the one or more light-emitting elements, based on the control signal, apply an output voltage of the light source driver as power of the one or more light-emitting elements in a turn-on period of the one or more light-emitting elements, and block the power of the one or more light-emitting elements by limiting output of the light source driver in a turn-off period of the one or more light-emitting elements.

According to certain embodiments, the electronic device further comprises a power supply module, wherein the light source driver comprises a circuit configured to generate the output voltage by boosting an input voltage from the power supply module, and provide the output voltage to the light-emitting element, wherein the at least one processor is configured to identify a pre-voltage value of reflected light received through the one or more light-receiving elements for a configured time, before configuring the control signal of the light source driver determine a drive current and a drive voltage of the one or more light-emitting elements, based on the identified pre-voltage value, and configure the control signal of the light source driver such that the input voltage applied to the light source driver is boosted to the determined drive voltage of the one or more light-emitting elements.

According to certain embodiments, the at least one processor is configured to identify an initial output voltage of the light source driver, and identify a compensation value for compensating for a difference between the identified initial output voltage and the determined drive voltage, and configure the control signal of the light source driver by applying the compensation value, and wherein the compensation value is at least one of a time parameter applied to the turn-on period or a voltage parameter applied to the input voltage of the light source driver.

According to certain embodiments, the at least one processor is configured to after configuring the control signal of the light source driver by applying the compensation value, identify the output voltage of the light source driver to which the compensation value has been applied, determine whether the identified output voltage satisfies the drive voltage reference of the one or more light-emitting elements, and based at least in part on a result of the determination, increase the compensation value in stages until the output voltage of the light source driver satisfies the drive voltage reference of the one or more light-emitting elements, so as to identify the output voltage of the light source driver.

According to certain embodiments, the at least one processor is configured to, in response to the turn-on/off timings of the one or more light-emitting elements, control the light source driver to operate in the turn-on period of the one or more light-emitting elements, and configure the light source driver not to operate in the turn-off period of the one or more light-emitting elements.

According to certain embodiments, the at least one processor is configured to in the turn-on period of the one or more light-emitting elements, transmit a high enable signal of the light source driver causing the light source driver to provide an output value to the one or more light-emitting elements, and in the turn-off period of the one or more light-emitting elements, transmit a low enable signal of the light source driver causing the light source driver to not output the output value.

According to certain embodiments, the at least one processor is configured to apply power of the light source driver in the turn-on period of the light-emitting element, and block power supply of the light source driver in the turn-off period of the one or more light-emitting elements to control whether to supply power supplied to the one or more light-emitting elements.

According to certain embodiments, the at least one processor is configured to monitor the output voltage of the light source driver, calculate whether a difference exists between the monitored output voltage of the light source driver and the determined drive voltage of the one or more light-emitting elements, and when the difference exists, apply a compensation value for compensating for the difference between the output voltage and the drive voltage, so as to configure the control signal of the light source driver.

According to certain embodiments, the at least one processor is configured to measure sensing information, based on a signal collected through the one or more light-receiving elements.

According to certain embodiments, an electronic device comprises an optical sensor module and a light source driver, wherein the optical sensor module comprises: one or more light-emitting elements; one or more light-receiving elements; a signal processing circuit configured to control driving of the light emitting elements and the one or more light-receiving elements; and at least one processor, the light source driver being configured to control power supply of the at least one light-emitting element, wherein the signal processing circuit is configured to, when the optical sensor module is driven, under a control of the at least one processor, configure a control signal of the light source driver in response to a light source of the one or more light-emitting elements and a turn-on/off timing signal of the one or more light-emitting elements according to a sensor measurement mode or a measurement function, wherein the signal processing circuit is configured to, based on the control signal, apply an output voltage obtained by boosting an input voltage through the light source driver as power of the one or more light-emitting elements in turn-on period of the one or more light-emitting elements, wherein the signal processing circuit is configured to block the power of the one or more light-emitting elements by limiting output of the light source driver in turn-off period of the one or more light-emitting elements, and wherein the signal processing circuit is configured to transmit a signal collected based on the one or more light-receiving elements to the at least one processor.

According to certain embodiments, the signal processing circuit is configured to identify a pre-voltage value of reflected light received through the one or more light-receiving elements for a configured time, before configuring the control signal of the light source driver, determine a drive current and a drive voltage of the one or more light-emitting elements, based on the identified pre-voltage value, configure the control signal of the light source driver such that the input voltage applied to the light source driver is boosted as much as the determined drive voltage of the one or more light-emitting elements, identify an initial output voltage boosted by the light source driver, identify a compensation value for compensating for a difference between the identified initial output voltage and the determined drive voltage, and configure the control signal of the light source driver by applying the compensation value.

According to certain embodiments, the signal processing circuit is configured to identify the compensation value, based at least in part on test data measured for each of the one or more light-emitting elements.

According to certain embodiments, the signal processing circuit is configured to in the turn-on period of the one or more light-emitting elements, transmit a high enable signal of the light source driver such that the light source driver provides an output value to the one or more light-emitting elements, and in the turn-off period of the one or more light-emitting elements, transmit a low enable signal of the light source driver such that the light source driver does not output the output value.

According to certain embodiments, the signal processing circuit is configured to apply power of the light source driver in the turn-on period of the one or more light-emitting elements, and block power supply of the light source driver in the turn-off period of the one or more light-emitting elements so as to control whether to supply power supplied to the one or more light-emitting elements, or wherein the signal processing circuit is configured to after configuring the control signal of the light source driver by applying the compensation value, identify the output voltage of the light source driver to which the compensation value has been applied, and determine whether the identified output voltage satisfies the drive voltage reference of the one or more light-emitting elements, and based on a result of the determination, increase the compensation value in stages until the output voltage of the light source driver satisfies the drive voltage reference of the one or more light-emitting elements, so as to identify the output voltage of the light source driver.

According to certain embodiments, the processor is configured to monitor the output voltage of the light source driver, calculate whether a difference exists between the monitored output voltage of the light source driver and the determined drive voltage of the one or more light-emitting elements, and when the difference exists, apply a compensation value for compensating for the difference between the output voltage and the drive voltage, so as to configure the control signal of the light source driver, and transmit the control signal to the signal processing circuit, receive a signal of the one or more light-receiving elements generated by the control signal transmitted from the signal processing circuit, and measure sensing information, based on the received signal of the one or more light-receiving elements.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

It should be appreciated that certain embodiments of the present disclosure and the terms used therein are not intended to limit the technological features set forth herein to particular embodiments and include various changes, equivalents, or replacements for a corresponding embodiment. Therefore, the scope of the present invention should be construed as including all changes or modifications derived based on the technical spirit of the present invention in addition to the embodiments disclosed herein are included in the scope of the present invention.

The invention claimed is:

1. An electronic device comprising:
   a housing;
   an optical sensor module disposed in the housing and comprising one or more light-emitting elements, and one or more light-receiving elements;
   a light source driver disposed in the housing and configured to control power supply of the one or more light-emitting elements;
   a power supply module; and
   at least one processor disposed in the housing and operatively connected to the optical sensor module and the light source driver,
   wherein the light source driver comprises a circuit configured to generate an output voltage by boosting an input voltage from the power supply module, and
   wherein the at least one processor is configured to:
   identify a light source of the one or more light-emitting elements and turn-on/off timings of the one or more light-emitting elements according to a sensor measurement mode or a measurement function when the optical sensor module is driven,
   configure a control signal of the light source driver such that the input voltage is boosted to the output voltage corresponding to a drive voltage of the one or more light-emitting elements in response to the identified turn-on/off timings of the one or more light-emitting elements,
   based on the control signal, apply the output voltage of the light source driver obtained by boosting the input voltage through the light source driver as power of the one or more light-emitting elements in a turn-on period of the one or more light-emitting elements, and
   control the light source driver to not apply the output voltage of the light source driver to the one or more light-emitting elements in a turn-off period of the one or more light-emitting elements.

2. The electronic device of claim 1,
   wherein the at least one processor is further configured to:
   identify a pre-voltage value of reflected light received through the one or more light-receiving elements for a configured time, before configuring the control signal of the light source driver, and
   determine a drive current and the drive voltage of the one or more light-emitting elements, based on the identified pre-voltage value.

3. The electronic device of claim 2, wherein the at least one processor is further configured to:
   identify an initial output voltage of the light source driver, and
   identify a compensation value for compensating for a difference between the identified initial output voltage and the drive voltage, and configure the control signal of the light source driver by applying the compensation value,
   wherein the compensation value is at least one of a time parameter applied to the turn-on period or a voltage parameter applied to the input voltage of the light source driver.

4. The electronic device of claim 3, wherein the at least one processor is further configured to:
   after configuring the control signal of the light source driver by applying the compensation value, identify the output voltage of the light source driver to which the compensation value has been applied,
   determine whether the identified output voltage satisfies a drive voltage reference of the one or more light-emitting elements, and
   based at least in part on a result of the determination, increase the compensation value in stages until the output voltage of the light source driver satisfies the drive voltage reference of the one or more light-emitting elements.

5. The electronic device of claim 1, wherein the at least one processor is further configured to, in response to the turn-on/off timings of the one or more light-emitting elements, control the light source driver to operate in the turn-on period of the one or more light-emitting elements, and configure the light source driver not to operate in the turn-off period of the one or more light-emitting elements.

6. The electronic device of claim 5, wherein the at least one processor is further configured to:
   in the turn-on period of the one or more light-emitting elements, transmit a high enable signal of the light source driver causing the light source driver to provide an output value to the one or more light-emitting elements, and
   in the turn-off period of the one or more light-emitting elements, transmit a low enable signal of the light source driver causing the light source driver to not output the output value.

7. The electronic device of claim 5, wherein the at least one processor is further configured to:
   apply power of the light source driver in the turn-on period of the light-emitting element, and
   block power supply of the light source driver in the turn-off period of the one or more light-emitting elements to control whether to supply power supplied to the one or more light-emitting elements.

8. The electronic device of claim 1, wherein the at least one processor is further configured to:
   monitor the output voltage of the light source driver,
   calculate whether a difference exists between the monitored output voltage of the light source driver and the determined drive voltage of the one or more light-emitting elements, and
   when the difference exists, apply a compensation value for compensating for the difference between the output voltage and the drive voltage, so as to configure the control signal of the light source driver.

9. The electronic device of claim 1, wherein the at least one processor is further configured to measure sensing information, based on a signal collected through the one or more light-receiving elements.

10. An electronic device comprising an optical sensor module and a light source driver,
    the optical sensor module comprising:
    one or more light-emitting elements;
    one or more light-receiving elements;
    a signal processing circuit configured to control driving of the one or more light emitting elements and the one or more light-receiving elements; and
    at least one processor,
    wherein the light source driver being configured to control power supply of the one or more light-emitting elements,
    wherein the signal processing circuit is configured to, when the optical sensor module is driven, under a control of the at least one processor, configure a control signal of the light source driver in response to a light source of the one or more light-emitting elements and a turn-on/off timing signal of the one or more light-emitting elements according to a sensor measurement mode or a measurement function, wherein the signal processing circuit is configured to, based on the control signal, apply an output voltage obtained by boosting an input voltage through the light source driver as power of the one or more light-emitting elements in a turn-on period of the one or more light-emitting elements, wherein the signal processing circuit is configured to block the power of the one or more light-emitting elements by limiting output of the light source driver in a turn-off period of the one or more light-emitting elements, and wherein the signal processing circuit is configured to transmit a signal collected based on the one or more light-receiving elements to the at least one processor.

11. The electronic device of claim 10, wherein the signal processing circuit is further configured to:
identify a pre-voltage value of reflected light received through the one or more light-receiving elements for a configured time, before configuring the control signal of the light source driver,
determine a drive current and a drive voltage of the one or more light-emitting elements, based on the identified pre-voltage value,
configure the control signal of the light source driver such that the input voltage applied to the light source driver is boosted as much as the determined drive voltage of the one or more light-emitting elements,
identify an initial output voltage boosted by the light source driver,
identify a compensation value for compensating for a difference between the identified initial output voltage and the determined drive voltage, and
configure the control signal of the light source driver by applying the compensation value.

12. The electronic device of claim 11, wherein the signal processing circuit is further configured to identify the compensation value, based at least in part on test data measured for each of the one or more light-emitting elements.

13. The electronic device of claim 11, wherein the signal processing circuit is further configured to:
in the turn-on period of the one or more light-emitting elements, transmit a high enable signal of the light source driver such that the light source driver provides an output value to the one or more light-emitting elements, and
in the turn-off period of the one or more light-emitting elements, transmit a low enable signal of the light source driver such that the light source driver does not output the output value.

14. The electronic device of claim 11, wherein the signal processing circuit is further configured to
apply power of the light source driver in the turn-on period of the one or more light-emitting elements, and block power supply of the light source driver in the turn-off period of the one or more light-emitting elements so as to control whether to supply power supplied to the one or more light-emitting elements, or
wherein the signal processing circuit is further configured to
after configuring the control signal of the light source driver by applying the compensation value, identify the output voltage of the light source driver to which the compensation value has been applied, and determine whether the identified output voltage satisfies the drive voltage reference of the one or more light-emitting elements, and
based on a result of the determination, increase the compensation value in stages until the output voltage of the light source driver satisfies the drive voltage reference of the one or more light-emitting elements.

15. The electronic device of claim 10, wherein the processor is further configured to:
monitor the output voltage of the light source driver,
calculate whether a difference exists between the monitored output voltage of the light source driver and the determined drive voltage of the one or more light-emitting elements, and when the difference exists, apply a compensation value for compensating for the difference between the output voltage and the drive voltage, so as to configure the control signal of the light source driver, and
transmit the control signal to the signal processing circuit, receive a signal of the one or more light-receiving elements generated by the control signal transmitted from the signal processing circuit, and measure sensing information, based on the received signal of the one or more light-receiving elements.

* * * * *